(12) United States Patent
Hinze et al.

(10) Patent No.: US 7,348,354 B2
(45) Date of Patent: Mar. 25, 2008

(54) CYCLOHEXYLUREA COMPOUNDS

(75) Inventors: Claudia Hinze, Aachen (DE); Hans Schick, Berlin (DE)

(73) Assignee: Gruenenthal GmbH, Aachen (DE)

( * ) Notice: Subject to any disclaimer, the term of this patent is extended or adjusted under 35 U.S.C. 154(b) by 441 days.

(21) Appl. No.: 11/126,161

(22) Filed: May 11, 2005

(65) Prior Publication Data

US 2005/0261358 A1    Nov. 24, 2005

Related U.S. Application Data

(63) Continuation of application No. PCT/EP03/12304, filed on Nov. 5, 2003.

(30) Foreign Application Priority Data

Nov. 11, 2002  (DE) ............................... 102 52 650

(51) Int. Cl.
A61K 31/404 (2006.01)
C07D 209/04 (2006.01)

(52) U.S. Cl. ............ 514/419; 548/469; 548/494; 564/305; 514/415

(58) Field of Classification Search ........... 548/469, 548/494; 564/305; 514/415, 419
See application file for complete search history.

(56) References Cited

U.S. PATENT DOCUMENTS 7,173,045 B2 * 2/2007 Sundermann et al. ....... 514/330

FOREIGN PATENT DOCUMENTS

| CH | 392498 | 5/1965 |
|----|--------|--------|
| DE | 19756036 | 6/1999 |
| DE | 69515465 | 8/2000 |
| WO | WO 01/83452 | 11/2001 |
| WO | WO 01/87838 | 11/2001 |
| WO | WO 02/055521 | 7/2002 |

OTHER PUBLICATIONS

Faud A. Abdulla et al., "Axotomy Reduces the Effect of Analgesic Opioids Yet Increases the Effect of Nociceptin on Dorsal Root Ganglion Neurons," The Journal of Neuroscience, Dec. 1, 1998, pp. 9685-9694, 18, 23, Society for Neuroscience.

Girolamo Calo et al., "Pharmacology of Nociceptin and its Receptor: A Novel Therapeutic Target," British Journal of Pharmacology, 2000, pp. 1261-1283, 129, Macmillan Publishers Ltd.

Francois Jenck et al., "Orphanin FQ Acts as an Anxiolytic to Attenuate Behavioral Responses to Stress," Proc. Natl. Acad. Sci., Dec. 1997, pp. 14854-14858, vol. 94, USA.

Michael A. King et al., "Spinal Analgesic Activity of Orphanin FQ/Nociceptin and its Fragments", Neuroscience Letters, 1997, pp. 113-116, 223, Elsevier Science Ireland Ltd.

Toshiya Manabe et al., "Facilitation of Long-Term Potentiation and Memory in Mice Lacking Nociceptin Receptors", Letters To Nature, Aug. 6, 1998, pp. 577-581, vol. 394, Macmillan Publishers Ltd.

Jean-Claude Meunier et al., "Isolation and Structure of the Endogenous Agonist of Opiod Receptor-Like ORL, Receptor," Letters to Nature, Oct. 12, 1995, pp. 532-535, vol. 377.

J.S. Mogil et al., "Orphanin FQ is a Functional Anti-Opioid Peptide", Neuroscience, 1996, pp. 333-337, vol. 75, No. 2, Elsevier Science Ltd., Great Britain.

Miyuki Nishi et al., "Unrestrained Nociceptive Response and DIsregulation of Hearing Ability in Mice Lacking the Nociceptin/OrphaninFQ Receptor," The EMBO Journal, 1997, pp. 1858-1864, vol. 16, No. 8, Oxford University Press.

Rainer K. Reinscheid et al., "Orphanin FQ: A Neuropeptide That Activates an Opioldlike G Protein-Coupled Receptor," Science, Nov. 3, 1995, pp. 792-794, vol. 270.

Daniel Lednicer et al., "4-Amino-4-arylcyclohexanones and Their Derivatives, a Novel Class of Analgestics", J. Med. Chem., 1980, pp. 424-430, 23.

* cited by examiner

Primary Examiner—Golam M. M. Shameem
(74) Attorney, Agent, or Firm—Crowell & Moring LLP

(57) ABSTRACT

Cyclohexylurea compounds corresponding to formula I

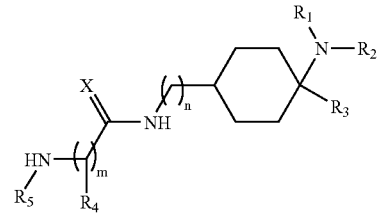

a method for producing them, pharmaceutical compositions containing them, and the use of such compounds as pharmaceutically active agents with nociceptin/ORL1 receptor system activity for treating pain or other conditions associated with the nociceptin/ORL1 receptor system.

25 Claims, No Drawings

CYCLOHEXYLUREA COMPOUNDS

CROSS REFERENCE TO RELATED APPLICATIONS

This application is a continuation of international patent application no. PCT/EP2003/012304, filed Nov. 5, 2003, designating the United States of America, and published in German as WO 2004/043909 A1 on May 27, 2004, the entire disclosure of which is incorporated herein by reference. Priority is claimed based on Federal Republic of Germany patent application no. DE 102 52 650.8, filed Nov. 11, 2002.

BACKGROUND OF THE INVENTION

The present invention relates to cyclohexylurea compounds, to processes for the production thereof, to pharmaceutical preparations containing these compounds and to the use of cyclohexylurea compounds for the production of pharmaceutical preparations.

The heptadecapeptide nociceptin is an endogenous ligand of the ORL1 (opioid-receptor-like) receptor (Meunier et al., Nature 377, 1995, p. 532-535), which belongs to the family of opioid receptors, may be found in many regions of the brain and spinal cord and exhibits a high affinity for the ORL1 receptor. The ORL1 receptor is homologous to the μ, κ and δ opioid receptors and the amino acid sequence of the nociceptin peptide exhibits a strong similarity to those of known opioid peptides. Nociceptin-induced activation of the receptor gives rise, via coupling with $G_{i/o}$ proteins, to inhibition of adenylate cyclase (Meunier et al., Nature 377, 1995, p. 532-535).

On intracerebroventricular administration, nociceptin peptide exhibits pronociceptive and hyperalgesic activity in various animal models (Reinscheid et al., Science 270, 1995, p. 792-794). These findings may be explained as inhibition of stress-induced analgesia (Mogil et al., Neuroscience 75, 1996, p. 333-337). In this connection, it has also been possible to demonstrate an anxiolytic activity of the nociceptin (Jenck et al., Proc. Natl. Acad. Sci. USA 94, 1997, 14854-14858).

On the other hand, it has also been possible to demonstrate an antinociceptive effect of nociceptin in various animal models, in particular on intrathecal administration. Nociceptin has an antinociceptive action in various pain models, for example in the murine tail-flick test (King et al., Neurosci. Lett., 223, 1997, 113-116). It has likewise proved possible to demonstrate an antinociceptive action of nociceptin in models of neuropathic pain, this action being of particular interest in that the activity of nociceptin increases after axotomy of spinal nerves. This is in contrast to classical opioids, whose activity decreases under these conditions (Abdulla and Smith, J. Neurosci., 18, 1998, p. 9685-9694).

The ORL1 receptor is also involved in the regulation of further physiological and pathophysiological processes. These include, inter alia, learning and memorisation (Manabe et al., Nature, 394, 1997, p. 577-581), hearing (Nishi et al., EMBO J., 16, 1997, p. 1858-1864) and many other processes. A review article by Calo et al. (Br. J. Pharmacol., 129, 2000, 1261-1283) provides an overview of the indications or biological processes in which the ORL1 receptor plays or could with a high level of probability play a role. The list includes the following: analgesia, stimulation and regulation of food intake, influence on μ agonists such as morphine, treatment of withdrawal symptoms, reduction of the addictive potential of opioids, anxiolysis, modulation of mobility, memory disorders, epilepsy; modulation of neurotransmitter release, in particular of glutamate, serotonin and dopamine, and thus of neurodegenerative diseases; influence on the cardiovascular system, initiation of erection, diuresis, antinatriuresis, electrolyte balance, arterial blood pressure, water retention diseases, intestinal motility (diarrhoea), relaxing effects on the respiratory tract, micturition reflex (urinary incontinence). The use of agonists and antagonists as anorectics, analgesics (also coadministered with opioids) or nootropics is also discussed.

Compounds which bind to the ORL1 receptor and activate or inhibit it have a correspondingly wide range of potential applications. In addition to this receptor, opioid receptors such as the μ receptor and other subtypes also play a major role, especially in pain therapy, but also in others of the stated indications. It is accordingly favourable if the compound also exhibits activity on these opioid receptors.

SUMMARY OF THE INVENTION

An object of the present invention was to provide pharmaceutical preparations which act on the nociceptin/ORL1 receptor system and are thus suitable for pharmaceutical preparations in particular for the treatment of the various conditions associated with this system in the prior art or for use in the indications stated therein.

The present invention accordingly provides cyclohexylurea compounds of the general formula I,

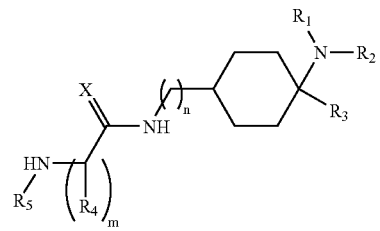

wherein
n=0-3,
m=0-2,
X=O or S (where m=0),
$R^1$ and $R^2$ are independently selected from the group consisting of H; $C_{1-8}$ alkyl and $C_{3-8}$ cycloalkyl, in each case saturated or unsaturated, branched or unbranched, mono- or polysubstituted or unsubstituted; aryl and heteroaryl, in each case mono- or polysubstituted or unsubstituted; and aryl, $C_{3-8}$ cycloalkyl or heteroaryl, in each case mono- or polysubstituted or unsubstituted, bound via $C_{1-3}$ alkylene, or
$R^1$ and $R^2$ together form a ring and represent $CH_2CH_2OCH_2CH_2$, $CH_2CH_2NR^6CH_2CH_2$ or $(CH_2)_{3-6}$, wherein
$R^6$ is selected from the group consisting of H; $C_{1-8}$ alkyl and $C_{3-8}$ cycloalkyl, in each case saturated or unsaturated, branched or unbranched, mono- or polysubstituted or unsubstituted; aryl and heteroaryl, in each case mono- or polysubstituted or unsubstituted; and aryl, $C_{3-8}$ cycloalkyl and heteroaryl bound via $C_{1-3}$ alkylene, in each case mono- or polysubstituted or unsubstituted;
$R^3$ is selected from the group consisting of $C_{1-8}$ alkyl and $C_{3-8}$ cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$ cycloalkyl and heteroaryl, in each case unsubstituted or mono- or polysubstituted, bound via a saturated or unsaturated, branched or unbranched, substituted or unsubstituted $C_{1-4}$ alkyl group;

$R^4$ is selected from the group consisting of H, $C_{1-8}$ alkyl, saturated or unsaturated, branched or unbranched, mono- or polysubstituted or unsubstituted; or —$(CH_2)_o$—W—$(CH_2)_p$—H wherein W=O, $NR_7$ or S;

o=0-3, and p=0-4 and wherein $R_7$ is selected from the group consisting of H, and $C_{1-8}$ alkyl, saturated or unsaturated, branched or unbranched, mono- or polysubstituted or unsubstituted;

$R^5$, if m≠0, is selected from the group consisting of:

—$(CH_2)_q R^{12}$,

—C(Y)-Z-$R^{12}$, and

—C(Y)—O-Z-$R^{12}$, wherein

Y=O, $CH_2$ or S,

Z=$C_{1-8}$ alkyl, saturated or unsaturated, branched or unbranched, mono- or polysubstituted or unsubstituted; or $(CH_2)_q$, wherein q=0-8, and $R^{12}$ is selected from the group consisting of H; $C_{3-8}$ cycloalkyl, aryl and heteroaryl, in each case unsubstituted or mono- or polysubstituted, or $R^5$, if m=0, is selected from the group consisting of $C_{3-8}$ cycloalkyl, aryl and heteroaryl, in each case unsubstituted or mono- or polysubstituted; and —$(CH_2)_q R^{12}$, wherein q=0-8, and $R^{12}$ is selected from the group consisting of H; $C_{3-8}$ cycloalkyl, aryl or heteroaryl, in each case unsubstituted or mono- or polysubstituted;

optionally in the form of the racemates thereof, the pure stereoisomers thereof, in particular enantiomers or diastereomers, or in the form of mixtures of the stereoisomers, in particular the enantiomers or diastereomers, in any desired mixing ratio; or in the form as prepared or in the form of the acids or bases thereof or in the form of the salts thereof, in particular the physiologically acceptable salts or salts of physiologically acceptable acids or cations; or in the form of the solvates thereof, in particular the hydrates.

All these compounds according to the invention bind well to the ORL1 receptor, but also to other opiate receptors.

For the purposes of the present invention alkyl or cycloalkyl radicals are taken to mean saturated and unsaturated (but not aromatic), branched, unbranched and cyclic hydrocarbons, which may be unsubstituted or mono- or polysubstituted. $C_{1-2}$ alkyl here denotes C1 or C2 alkyl, $C_{1-3}$ alkyl denotes C1, C2 or C3 alkyl, $C_{1-4}$ alkyl denotes C1, C2, C3 or C4 alkyl, $C_{1-5}$ alkyl denotes C1, C2, C3, C4 or C5 alkyl, $C_{1-6}$ alkyl denotes C1, C2, C3, C4, C5 or C6 alkyl, $C_{1-7}$ alkyl denotes C1, C2, C3, C4, C5, C6 or C7 alkyl, $C_{1-8}$ alkyl denotes C1, C2, C3, C4, C5, C6, C7 or C8 alkyl, $C_{1-10}$ alkyl denotes C1, C2, C3, C4, C5, C6, C7, C8, C9 or C10 alkyl and $C_{1-18}$ alkyl denotes C1, C2, C3, C4, C5, C6, C7, C8, C9, C10, C11, C12, C13, C14, C15, C16, C17 or C18 alkyl. $C_{3-4}$ cycloalkyl furthermore denotes C3 or C4 cycloalkyl, $C_{3-5}$ cycloalkyl denotes C3, C4 or C5 cycloalkyl, $C_{3-6}$ cycloalkyl denotes C3, C4, C5 or C6 cycloalkyl, $C_{3-7}$ cycloalkyl denotes C3, C4, C5, C6 or C7 cycloalkyl, $C_{3-8}$ cycloalkyl denotes C3, C4, C5, C6, C7 or C8 cycloalkyl, $C_{4-5}$ cycloalkyl denotes C4 or C5 cycloalkyl, $C_{4-6}$ cycloalkyl denotes C4, C5 or C6 cycloalkyl, $C_{4-7}$ cycloalkyl denotes C4, C5, C6 or C7 cycloalkyl, $C_{5-6}$ cycloalkyl denotes C5 or C6 cycloalkyl and $C_{5-7}$ cycloalkyl denotes C5, C6 or C7 cycloalkyl. With regard to cycloalkyl, the term also includes saturated cycloalkyls in which one or 2 carbon atoms are replaced by a heteroatom, S, N or O. The term cycloalkyl in particular, however, also includes mono- or polyunsaturated, preferably monounsaturated, cycloalkyl without a heteroatom in the ring, provided that the cycloalkyl does not constitute an aromatic system. The alkyl or cycloalkyl radicals are preferably methyl, ethyl, vinyl (ethenyl), propyl, allyl (2-propenyl), 1-propynyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, as well as adamantyl, $CHF_2$, $CF_3$ or $CH_2OH$ and pyrazolinone, oxopyrazolinone, [1,4]-dioxane or dioxolane.

In relation to alkyl and cycloalkyl, it should be understood that, unless explicitly stated otherwise, for the purposes of the present invention, substituted means the substitution of at least one hydrogen atom (optionally also a plurality of hydrogen atoms) by F, Cl, Br, I, $NH_2$, SH or OH, wherein, in the case of repeated substitution, "polysubstituted" or "substituted" should be taken to mean that substitution is performed repeatedly both on different and the same C atoms with the same or different substituents, for example three times on the same C atom as in case of $CF_3$ or on different sites as in the case of —CH(OH)—CH=CH—$CHCl_2$. Examples of particularly preferred substituents in this context include F, Cl and OH. With regard to cycloalkyl, the hydrogen atom may also be replaced by $OC_{1-3}$ alkyl or $C_{1-3}$ alkyl (in each case mono- or polysubstituted or unsubstituted), in particular methyl, ethyl, n-propyl, i-propyl, $CF_3$, methoxy or ethoxy.

The term $(CH_2)_{3-6}$ should be taken to mean —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and $(CH_2)_{1-4}$ should be taken to mean —$CH_2$—, —$CH_2$—$CH_2$—, —$CH_2$—$CH_2$—$CH_2$— and —$CH_2$—$CH_2$—$CH_2$—$CH_2$—, while $(CH_2)_{4-5}$ should be taken to mean —$CH_2$—$CH_2$—$CH_2$—$CH_2$— and —$CH_2$—$CH_2$—$CH_2$—$CH_2$—$CH_2$— etc.

An aryl radical is taken to mean ring systems comprising at least one aromatic ring, but without a heteroatom in even one of the rings. Examples include phenyl, naphthyl, fluoranthenyl, fluorenyl, tetralinyl or indanyl, in particular 9H fluorenyl or anthracenyl radicals, which may be unsubstituted or mono- or polysubstituted.

A heteroaryl radical is taken to mean heterocyclic ring systems comprising at least one unsaturated ring, which contain one or more heteroatoms from the group comprising nitrogen, oxygen and/or sulfur and may also be mono- or polysubstituted. Examples from the group of heteroaryls which may be mentioned are furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

In relation to aryl and heteroaryl, substituted is taken to mean the substitution of the aryl or heteroaryl with $R^{22}$, $OR^{22}$, a halogen, preferably F and/or Cl, a $CF_3$, a CN, an $NO_2$, an $NR^{23}R^{24}$, a $C_{1-6}$ alkyl (saturated), a $C_{1-6}$ alkoxy, a $C_{3-8}$ cycloalkoxy, a $C_{3-8}$ cycloalkyl or a $C_{2-6}$ alkylene.

The radical $R^{22}$ in this context denotes H, a $C_{1-10}$ alkyl, preferably a $C_{1-6}$ alkyl, an aryl or heteroaryl or an aryl or heteroaryl radical bound via $C_{1-3}$ alkyl, saturated or unsaturated, or a $C_{1-3}$ alkylene group, wherein these aryl and heteroaryl radicals may not themselves be substituted with aryl or heteroaryl radicals.

The radicals $R^{23}$ and $R^{24}$, which may be the same or different, denote H, a $C_{1-10}$ alkyl, preferably a $C_{1-6}$ alkyl, an aryl, a heteroaryl or an aryl or heteroaryl bound via $C_{1-3}$ alkyl, saturated or unsaturated, or a $C_{1-3}$ alkylene group, wherein these aryl and heteroaryl radicals may not themselves be substituted with aryl or heteroaryl radicals, or the radicals $R^{23}$ and $R^{24}$ together represent $CH_2CH_2OCH_2CH_2$, $CH_2CH_2NR^{25}CH_2CH_2$ or $(CH_2)_{3-6}$.

The radical $R^{25}$ denotes H, a $C_{1-10}$ alkyl, preferably a $C_{1-6}$ alkyl, an aryl or heteroaryl radical or denotes an aryl or heteroaryl radical bound via $C_{1-3}$ alkyl, saturated or unsaturated, or a $C_{1-3}$ alkylene group, wherein these aryl and heteroaryl radicals may not themselves be substituted with aryl or heteroaryl radicals.

The term salt should be taken to mean any form of the active substance according to the invention, in which the latter assumes an ionic form or bears a charge and is coupled with a counterion (a cation or anion) or is in solution. These should also be taken to mean complexes of the active substance with other molecules and ions, in particular complexes which are complexed by means of ionic interactions. These should in particular be taken to mean (and this is also a preferred embodiment of the present invention) physiologically acceptable salts, in particular physiologically acceptable salts with cations or bases and physiologically acceptable salts with anions or acids or also a salt formed with a physiologically acceptable acid or a physiologically acceptable cation.

For the purposes of the present invention, a physiologically acceptable salt with anions or acids is taken to mean salts of at least one of the compounds according to the invention, usually protonated, for example on the nitrogen, as the cation with at least one anion, which is physiologically acceptable, in particular for use in humans and/or mammals. In particular, for the purposes of the present invention, the physiologically acceptable salt is taken to be the salt formed with a physiologically acceptable acid, namely salts of the particular active substance with inorganic or organic acids which are physiologically acceptable, in particular for use in humans and/or mammals. Examples of physiologically acceptable salts of specific acids include the salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1b$^6$-benzo[d]isothiazol-3-one (saccharic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt and the citrate salt are particularly preferred.

For the purposes of the present invention, a salt formed with a physiologically acceptable acid should be taken to mean salts of the particular active ingredient with inorganic or organic acids which are physiologically acceptable, in particular for use in humans and/or mammals. The hydrochloride or citrate is particularly preferred. Examples of physiologically acceptable acids include hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro1λ$^6$-benzo[d]isothiazol-3-one (saccharic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid.

For the purposes of the present invention, a physiologically acceptable salt with cations or bases is taken to mean salts of at least one of the compounds according to the invention, usually a (deprotonated) acid, as the anion with at least one, preferably inorganic, cation, which is physiologically acceptable, in particular for use in humans and/or mammals. Particularly preferred are salts of the alkali and alkaline earth metals, as are those with $NH_4^+$, most particularly (mono-) or (di-)sodium, (mono-) or (di-)potassium, magnesium or calcium salts.

For the purposes of the present invention, a salt formed with a physiologically acceptable cation should be taken to mean salts of at least one of the particular compounds as the anion with at least one inorganic cation which is physiologically acceptable, in particular for use in humans and/or mammals. Particularly preferred are salts of the alkali and alkaline earth metals, as are those of $NH_4^+$, most particularly (mono-) or (di-)sodium, (mono-) or (di-)potassium, magnesium or calcium salts.

In a preferred embodiment of the cyclohexylurea compounds according to the invention:
$R^1$ and $R^2$ are independently selected from the group consisting of H and $C_{1-8}$ alkyl, saturated or unsaturated, branched or unbranched, mono- or polysubstituted or unsubstituted; or
$R^1$ and $R^2$ together form a ring and represent $CH_2CH_2OCH_2CH_2$, $CH_2CH_2NR^6CH_2CH_2$ or $(CH_2)_{3-6}$, wherein
$R^6$ is selected from the group consisting of H and $C_{1-8}$ alkyl, saturated or unsaturated, branched or unbranched, mono- or polysubstituted or unsubstituted.

Preferably $R^1$ and $R^2$ are independently selected from the group consisting of H and $C_{1-4}$ alkyl, saturated or unsaturated, branched or unbranched, mono- or polysubstituted or unsubstituted, or $R^1$ and $R^2$ together form a ring and represent $(CH_2)_{4-5}$. In particular, $R^1$ and $R^2$ are independently selected from the group consisting of H, methyl and ethyl.

In another preferred embodiment of the cyclohexylurea compounds according to the invention, $R^3$ is selected from the group consisting of $C_{3-8}$ cycloalkyl, aryl and heteroaryl, in each case unsubstituted or mono- or polysubstituted; and aryl, $C_{3-8}$ cycloalkyl or heteroaryl, in each case unsubstituted or mono- or polysubstituted, bound via a saturated or unsaturated, unbranched, substituted or unsubstituted $C_{1-2}$ alkyl group. Preferably $R^3$ is selected from the group consisting of $C_{5-6}$ cycloalkyl, phenyl, naphthyl, anthracenyl, thiophenyl, benzothiophenyl, furyl, benzofuranyl, benzodioxolanyl, indolyl, indanyl, benzodioxanyl, pyrrolyl, pyrimidiyl or pyrazinyl, in each case unsubstituted or mono- or polysubstituted; $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, in each case unsubstituted or mono- or polysubstituted, bound via a saturated, unbranched $C_{1-2}$ alkyl group. In particular, $R^3$ is selected from the group consisting of phenyl, furyl, thiophenyl, cyclohexanyl, naphthyl, benzofuranyl, indolyl, indanyl, benzodioxanyl, benzodioxolanyl, pyrrolyl, pyrimidiyl, pyrazinyl or benzothiophenyl, in each case unsubstituted or mono- or polysubstituted; phenyl, furyl or thiophenyl, in each case unsubstituted or mono- or polysubstituted, bound via a saturated, unbranched $C_{1-2}$ alkyl group.

In yet another preferred embodiment of the invention, $R^4$ is selected from the group consisting of H and $C_{1-8}$ alkyl, saturated or unsaturated, branched or unbranched, mono- or polysubstituted or unsubstituted, preferably H, $CH_3$ or $C_2H_5$.

In still another preferred embodiment of the cyclohexylurea compounds according to the invention, $R^{12}$ is selected from the group consisting of H; cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidiyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl and quinazolinyl, in each case unsubstituted or mono- or polysubstituted. In particular, $R^{12}$ is selected from the group consisting of H; cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl and pyrimidiyl, in each case unsubstituted or mono- or polysubstituted.

The present invention particularly preferably provides cyclohexylurea compounds corresponding to the formula I,

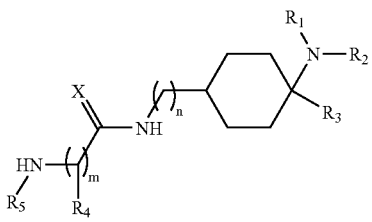

in which
$R_1$ and $R_2$ are independently selected from the group consisting of H, $CH_3$, $C_2H_5$ and CHO, particularly preferably H or $CH_3$;
$R_3$ is selected from the group consisting of indolyl, pyridyl, thienyl, pyrrolyl, phenyl, benzyl and phenethyl, in each case unsubstituted or mono- or polysubstituted on the ring, particularly preferably phenyl which is unsubstituted or mono-substituted on the ring; benzyl, phenethyl, indolyl, pyridyl, thienyl, or pyrrolyl; and
$R_4$ is selected from the group consisting of H, $CH_3$, $C_2H_5$, n-propyl, i-propyl, n-butyl, i-butyl or t-butyl.

$R_3$ is especially preferably selected from the group consisting of phenyl, benzyl, phenethyl, o-fluorophenyl, m-fluorophenyl, p-fluorophenyl, o-chlorophenyl, p-chlorophenyl, m-chlorophenyl, o-bromophenyl, m-bromophenyl, p-bromophenyl, o-iodophenyl, m-iodophenyl, p-iodophenyl, o-aminophenyl, m-aminophenyl, p-aminophenyl, o-methylphenyl, m-methylphenyl, p-methylphenyl, o-methoxyphenyl, m-methoxyphenyl, p-methoxyphenyl, o-ethylphenyl, m-ethylphenyl, p-ethylphenyl, o-ethoxyphenyl, m-ethoxyphenyl, p-ethoxyphenyl, o-hydroxyphenyl, m-hydroxyphenyl or p-hydroxyphenyl; indolyl, pyridyl, thienyl, and pyrrolyl.

With regard to this particularly preferred subject matter, it is particularly preferred if, for the preferred 4-aminomethyl-1-aryl-cyclohexylamine compounds according to the invention $R_5$, when m≠0, is selected from the group consisting of —$(CH_2)_q R^{12}$, —C(Y)-Z-$R^{12}$ and —C(Y)—O-Z-$R^{12}$, wherein Y=O, and Z=$C_{1-6}$ alkyl, saturated or unsaturated, branched or unbranched, mono- or polysubstituted or unsubstituted, or $(CH_2)_q$, in which q=0-6.

With regard to this particularly preferred subject matter, it is particularly preferred if, for the preferred 4-aminomethyl-1-aryl-cyclohexylamine compounds according to the invention, $R_5$, when m=0, is —$(CH_2)_q R_{12}$, in which q=0-6.

With regard to this particularly preferred subject matter, it is particularly preferred if, for the preferred 4-aminomethyl-1-aryl-cyclohexylamine compounds according to the invention, $R^{12}$ is selected from the group consisting of H; cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidiyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl and quinazolinyl, in each case unsubstituted or mono- or polysubstituted. Particularly preferably, $R^{12}$ is selected from the group consisting of H; cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl and pyrimidiyl, in each case unsubstituted or mono- or polysubstituted. Very particularly preferably $R^{12}$ is selected from the group consisting of phenyl and indolyl, in each case unsubstituted, mono- or polysubstituted. Unsubstituted phenyl or indolyl or phenyl monosubstituted in para-position with methyl, methoxy, chlorine, fluorine or $CF_3$, or indolyl monosubstituted in position 5 with methyl, methoxy, chlorine, fluorine or $CF_3$ are especially preferably preferred according to the invention.

Very particularly preferred 4-substituted cyclohexylurea compounds according to the invention are selected from the group consisting of:
1-(4-dimethylamino-4-phenylcyclohexyl)-3-(3-phenylpropyl)urea hydrochloride (more nonpolar and more polar diastereoisomer);
1-(4-dimethylamino-4-phenylcyclohexyl)-3-[2-1H-indol-3-yl)ethyl]urea hydrochloride (more nonpolar and more polar diastereoisomer);
N-[(4-dimethylamino-4-phenylcyclohexylcarbamoyl)methyl]-3-(1H-indol-3-yl)butyramide hydrochloride (more nonpolar and more polar diastereoisomer);
5-(1H-indol-3-yl)-pentanoic acid [(4-dimethylamino-4-phenylcyclohexylcarbamoyl)methyl]amide hydrochloride (more nonpolar and more polar diastereoisomer);
6-(1H-indol-3-yl)hexanoic acid [(4-dimethylamino-4-phenylcyclohexylcarbamoyl)-methyl]-amide hydrochloride (more nonpolar and more polar diastereoisomer);
N-[(4-dimethylamino-4-phenylcyclohexylcarbamoyl)methyl]-3-(1H-indol-3-yl)propionamide hydrochloride (more nonpolar and more polar diastereoisomer);
N-(4-dimethylamino-4-phenylcyclohexyl)-2-(2-1H-indol-3-ylacetylamino)-propionamide hydrochloride (more nonpolar and more polar diastereoisomer);
2-(2-1H-indol-3-ylacetylamino)-4-methylpentanoic acid (4-dimethylamino-4-phenylcyclohexyl)amide hydrochloride (more nonpolar and more polar diastereoisomer);

1-(4-dimethylamino-4-phenylcyclohexyl)-3-[2-(1H-indol-3-yl)-1-methyl-ethyl]-urea hydrochloride (more nonpolar and more polar diastereoisomer);
1-(4-dimethylamino-4-phenylcyclohexyl)-3-[2-(5-fluoro-1H-indol-3-yl)ethyl]-urea hydrochloride (more nonpolar and more polar diastereoisomer);
1-(4-dimethylamino-4-phenylcyclohexylmethyl)-3-[2-(1H-indol-3-yl)ethyl]-urea hydrochloride (more nonpolar and more polar diastereoisomer);
1-(4-dimethylamino-4-phenylcyclohexylmethyl)-3-(3-phenylpropyl)urea hydrochloride (more nonpolar and more polar diastereoisomer);
1-(4-dimethylamino-4-phenylcyclohexylmethyl)-3-[2-(1H-indol-3-yl)-1-methylethyl]-urea hydrochloride (more nonpolar and more polar diastereoisomer);
1-(4-dimethylamino-4-phenylcyclohexylmethyl)-3-[2-(5-fluoro-1H-indol-3-yl)ethyl]urea citrate (more nonpolar and more polar diastereoisomer);
1-[3-(4-dimethylamino-4-phenyl-cyclohexyl)-propyl]-3-[2-(1H-indol-3-yl)-ethyl]-urea (more nonpolar and more polar diastereoisomer);
1-(4-dimethylamino-4-phenylcyclohexyl)-3-(4-phenyl-propyl)thiourea citrate (more nonpolar and more polar diastereoisomer);
1-(4-dimethylamino-4-phenylcyclohexyl)-3-[2-(1H-indol-3-yl)methyl-ethyl]thiourea citrate (more nonpolar and more polar diastereoisomer);
1-[3-(4-dimethylamino-4-phenyl-cyclohexyl)-propyl]-3-[2-(1H-indol-3-yl)-ethyl]-urea (more nonpolar and more polar diastereoisomer);
1-(4-dimethylamino-4-phenylcyclohexylmethyl)-3-[2-(1H-indol-3-yl)ethyl]-thiourea citrate (more nonpolar and more polar diastereoisomer);
1-(4-dimethylamino-4-phenylcyclohexylmethyl)-3-[2-(1H-indol-3-yl)-1-methylethyl]thiourea citrate (more nonpolar and more polar diastereoisomer);
2-[3-(4-dimethylamino-4-phenylcyclohexylmethyl)thioureido]-3-(1H-indol-3-yl)propionic acid methyl ester citrate (more nonpolar and more polar diastereoisomer);
1-[2-(4-dimethylamino-4-phenylcyclohexyl)ethyl]-3-[2-(1H-indol-3-yl)-ethyl]thiourea hydrochloride (more nonpolar diastereoisomer); and
1-[2-(4-dimethylamino-4-phenylcyclohexyl)ethyl]-3-[2-(1H-indol-3-yl)-ethyl]thiourea citrate (more polar diastereoisomer).

The substances according to the invention are toxicologically safe, so they are suitable as a pharmaceutical active ingredient in pharmaceutical preparations. The present invention accordingly also provides pharmaceutical preparations containing at least one cyclohexylurea compound according to the invention.

In addition to at least one cyclohexylurea compound according to the invention, the pharmaceutical compositions according to the invention also contain suitable additives and/or auxiliary substances, which accordingly include matrix materials, fillers, solvents, diluents, dyes and/or binders and may be administered as liquid dosage forms in the form of solutions for injection, drops or succi, as semisolid dosage forms in the form of granules, tablets, pellets, patches, capsules, dressings or aerosols. Selection of the auxiliary substances etc. and the quantities thereof to be used depend on whether the pharmaceutical preparation is to be administered orally, perorally, parenterally, intravenously, intraperitoneally, intradermally, intramuscularly, intranasally, buccally, rectally or topically, for example onto the skin or the mucous membranes or into the eyes. Preparations in the form of tablets, coated tablets, capsules, granules, drops, succi and syrups are suitable for oral administration, while solutions, suspensions, easily reconstitutible dried preparations and sprays are suitable for parenteral, topical and inhalatory administration. Cyclohexylurea compounds according to the invention in a depot in dissolved form or in a dressing, optionally with the addition of skin penetration promoters, are suitable percutaneous administration preparations. Orally or percutaneously administrable formulations may release the cyclohexylurea compounds according to the invention in a delayed manner. In principle, other active ingredients known to the person skilled in the art may be added to the pharmaceutical preparations according to the invention.

The quantity of active substance to be administered to the patient varies depending on patient weight, mode of administration, the indication and the severity of the condition. Typically, 0.005 to 1000 mg/kg, preferably 0.05 to 5 mg/kg, of at least one cyclohexylurea compound according to the invention are administered.

For all of the above forms of pharmaceutical preparations according to the invention, it is particularly preferable for the pharmaceutical preparation to contain, in addition to at least one cyclohexylurea compound, a further active ingredient, in particular an opioid, preferably a strong opioid, in particular morphine, or an anaesthetic, preferably hexobarbital or halothane.

In a preferred form of the pharmaceutical preparation, a cyclohexylurea compound according to the invention is present therein as a pure diastereomer and/or enantiomer, as a racemate or as a non-equimolar or equimolar mixture of the diastereomers and/or enantiomers.

As stated above in background of the invention section, the ORL1 receptor has in particular been identified in pain phenomena. Accordingly cyclohexylurea compounds according to the invention may be used to produce a pharmaceutical preparation for the treatment of pain, in particular of acute, neuropathic or chronic pain. The invention therefore further provides the use of a cyclohexylurea compound according to the invention to produce a pharmaceutical preparation for the treatment of pain, in particular of acute, visceral, neuropathic or chronic pain.

The invention also embraces the use of a cyclohexylurea compound according to the invention for the production of a pharmaceutical preparation for the treatment of anxiety, stress and stress-related syndromes, depression, epilepsy, Alzheimer's disease, senile dementia, general cognitive dysfunction, learning and memory disorders (as a nootropic), withdrawal symptoms, abuse of and/or dependency on alcohol and/or drugs and/or medicines, sexual dysfunction, cardiovascular diseases, hypotension, hypertension, tinnitus, pruritus, migraine, hardness of hearing, insufficient intestinal motility, eating disorders, anorexia, obesity, locomotive disorders, diarrhoea, cachexia, urinary incontinence or as a muscle relaxant, anticonvulsive or anaesthetic or for coadministration on treatment with an opioid analgesic or with an anaesthetic, for diuresis or antinatriuresis, anxiolysis, for modulation of mobility, for modulation of neurotransmitter release and treatment of neurodegenerative diseases associated therewith, for the treatment of withdrawal symptoms and/or the reduction of the addictive potential of opioids.

It may here be preferred in one of the above-stated uses if a cyclohexylurea compound which is used is present in the form of a pure diastereomer and/or enantiomer, of a racemate or of a non-equimolar or equimolar mixture of the diastereomers and/or enantiomers.

The present invention also provides a process or method for treating one or more of the foregoing indications, or for treating a non-human mammal or a human for pain, in particular chronic pain, by administration of a therapeutically effective dose of a cyclohexylurea compound according to the invention or a pharmaceutical preparation according to the invention.

The present invention also provides processes for producing the cyclohexylurea compounds according to the invention.

A first process for the production of the cyclohexylurea compounds of formula I comprises the steps of:
a1) for compounds in which n=0, conversion of a 4-aminocyclohexanone by oxime formation and subsequent reduction or by reductive amination into the corresponding 4-aminocyclohexylamine (see also general synthesis scheme (I) below),
a2) for compounds in which n=1, reaction of a 4-aminocyclohexanone with the reaction product of alkoxymethyl triphenylphosphonium halide and a strong base to yield 4-aminocyclohexanecarbaldehyde, and subsequent reductive amination or oxime formation and successive reduction to yield 4-aminocyclohexylmethylamine (see also general synthesis scheme (III) below);
a3) for compounds in which n=2, reaction of a 4-aminocyclohexanone with the reaction product of cyanomethylphosphonic acid dialkyl ester and a strong base to yield the α,β-unsaturated nitrile, which is then reduced to yield 4-aminocyclohexylethylamine (see also general synthesis scheme (VII) below);
a4) for compounds in which n=3, reaction of a 4-aminocyclohexanecarbaldehyde obtained as described in a2) for further chain extension with the reaction product of cyanomethanephosphonic acid dialkyl ester and a strong base to yield α,β-unsaturated nitrile, and subsequent reduction of the resultant α,β-unsaturated nitrile to yield the amine (see also general synthesis scheme (IX) below);
b) reaction of the amine formed in step a1), a2), a3) or a4) with an activated carbonic acid compound in the presence of a base to yield the carbamic acid ester;
c) reaction of the carbamic acid ester obtained in step b) with amines of the formula $R_5$—$NH_2$ to yield cyclohexylurea compounds of the formula I with m=0.

A process for the production of cyclohexylurea compounds of the formula I in which m≠0 and $R^5$ is selected from the group consisting of —C(Y)-Z-$R^{12}$ or —C(Y)—O-Z-$R^{12}$ with Y=O or S is characterised in that an amine produced according to step a1, a2), a3) or a4) of the process described above, is acylated with a Boc amino acid compound activated on the carbonyl terminus, then the Boc protecting group is eliminated under acidic conditions and the deprotected amino group is then acylated with an activated carboxylic acid compound (see also general synthesis scheme (V) below).

A further process for the production of cyclohexylurea compounds of the formula I is characterised in that an amine of the formula $R_5$—$NH_2$ is reacted with an activated carbonic acid compound to yield a carbamic acid ester and then the reaction with an amine obtained according to step a1, a2), a3) or a4) of the process described above to yield a cyclohexylurea compound of the formula I with m=0 is performed (see also general synthesis schemes (II), (IV) and (VIII) below).

A process for the production of cyclohexylurea compounds of the formula I with m≠0 is characterised in that 4-aminocyclohexylamines obtained according to step a1, a2), a3) or a4) of the process described above are acylated according to the following synthesis scheme (VI) with amino acid compounds activated on the carboxyl terminus.

An alternative process for the production of cyclohexylurea compounds of the formula I, in which X=O or S and m=0, is characterised in that an amine produced according to step a1), a2), a3) or a4) of the process described above is reacted with an isocyanate of the formula OCN—$R_5$ or with an isothiocyanate of the formula SCN—$R_5$ to yield the cyclohexylurea compound of the formula I.

Further details are given in the following description and the Examples, in which $R_1$, $R_2$, $R_3$, $R_4$, $R_5$ have the meanings stated for compounds according to the invention of the formula I, and $R_{01}$ and $R_{02}$ are independently selected from the group consisting of a protecting group or the groups stated for $R_1$ and $R_2$ for compounds according to the invention of formula I:

General Synthesis Scheme, Cyclohexylureas (I):

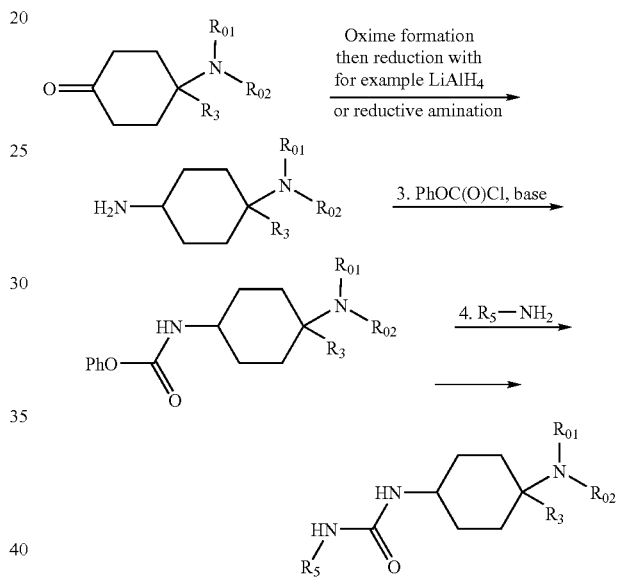

The production of suitable 4-aminocyclohexanones is known from the literature (Lednicer et al., J. Med. Chem., 23, 1980, 424-430; WO 0290317).

A 4-aminocyclohexanone may be converted under conditions known to persons skilled in the art, for example, with hydroxylamine hydrochloride in dry pyridine and absolute ethanol, into the oxime. The latter may then be converted into the amine using conventional reduction methods, for example by reduction with Devarda's alloy (Cu, Al, Zn); preferably with nickel(II) halide and sodium hydridoborate; or particularly preferably with complex hydrides (for example lithium alanate).

Alternatively, the ketone may be reductively aminated using methods known to the person skilled in the art, for example with ammonium acetate and sodium cyanoborohydride. The 4-aminocyclohexylamine intermediates formed are reacted with activated carbonic acid compounds such as for example with chloroformic acid phenyl ester, chloroformic acid p-nitrophenyl ester or the like and a suitable base, for example pyridine or DMAP. The intermediates obtained, for example carbamic acid esters, are reacted with primary amines to yield the corresponding ureas.

Alternative Synthesis Scheme, Cyclohexylureas (II):

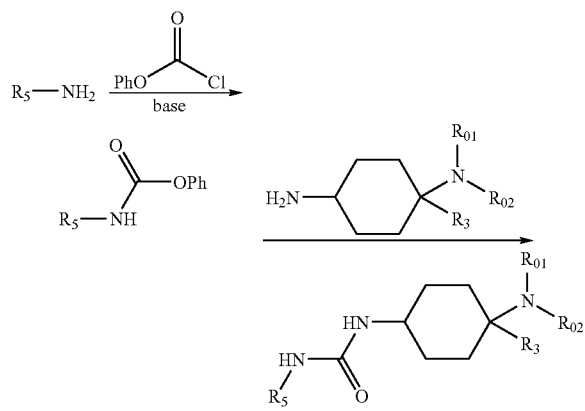

Primary amines are reacted with activated carbonic acid compounds, such as for example with chloroformic acid phenyl ester, chloroformic acid p-nitrophenyl ester or the like and a suitable base, for example pyridine or DMAP. The resulting intermediates, for example carbamic acid esters, are reacted with the 4-aminocyclohexylamine intermediates known from process I to yield the corresponding ureas.

General Synthesis Scheme, Cyclohexymethylureas (III):

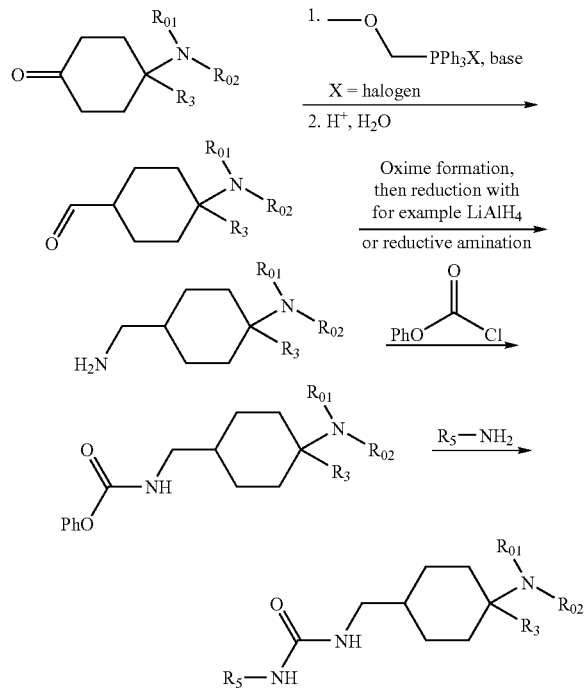

Methoxymethyltriphenylphosphonium halide is reacted first with a strong base, for example sodium hydride or butyllithium, then with a 4-aminocyclohexanone and the methyl vinyl ether formed as an intermediate is converted under acidic aqueous conditions, for example with hydrochloric acid or sulfuric acid, into the corresponding 4-aminocyclohexanecarbaldehyde conversion. The latter is converted into the oxime under conditions known to the person skilled in the art. The latter may then be converted into the corresponding 4-aminomethylcyclohexylamine using conventional reduction methods, for example by reduction with Devarda's alloy (Cu, Al, Zn); or preferably with nickel(II) halide and sodium hydridoborate; or particularly preferably with complex hydrides (for example lithium alanate).

Alternatively, the ketone may be reductively aminated using methods known to persons skilled in the art, for example with ammonium acetate and sodium cyanoborohydride.

The resulting cyclohexylmethylamine intermediates are reacted with activated carbonic acid compounds, such as for example with chloroformic acid phenyl ester, chloroformic acid p-nitrophenyl ester or the like, and a suitable base, for example pyridine or DMAP. The resulting intermediates, for example carbamic acid esters, are reacted with primary amines to yield the corresponding ureas.

Alternative Synthesis Scheme, Cyclohexylmethylureas (IV):

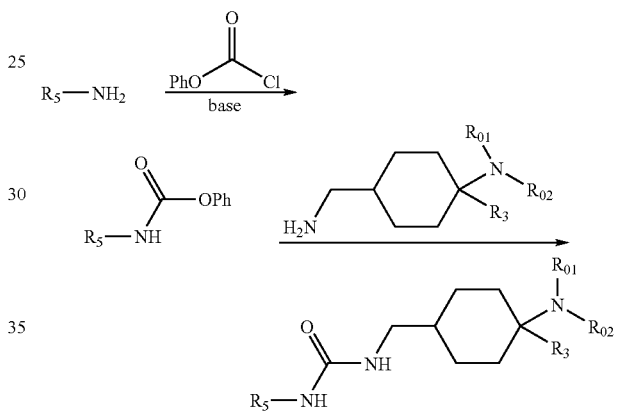

Primary amines are reacted with activated carbonic acid compounds, such as for example with chloroformic acid phenyl ester, chloroformic acid p-nitrophenyl ester or the like and a suitable base, for example pyridine or DMAP. The resulting intermediates, for example carbamic acid esters, are reacted with the 4-aminomethylcyclohexylamine intermediates known from process III to yield the corresponding ureas.

General Synthesis Scheme, Acylamino Acid Cyclohexylamide Compounds (V):

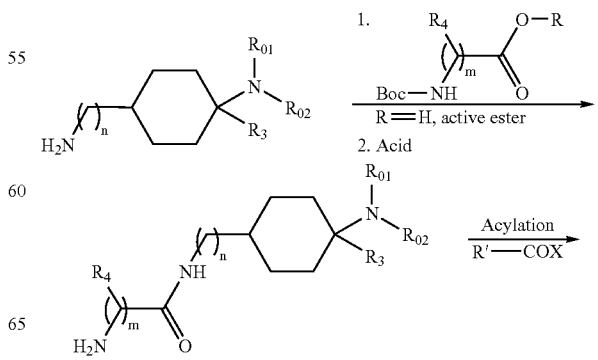

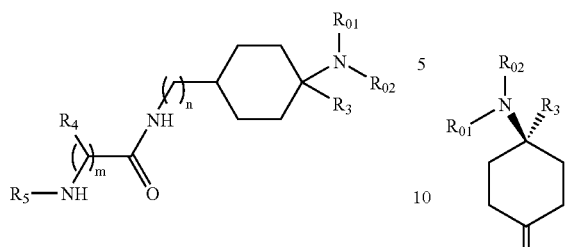

The 4-aminocyclohexyl(alkyl)amine intermediates (described in synthesis schemes I, III or VII) are acylated with Boc amino acid compounds (Boc=tert.-butyloxycarbonyl) activated on the carboxyl terminus, these compounds being produced in situ using conventional peptide coupling methods known from the literature (Miklos Bodanszky, Agnes Bodanszky, *The Practice of Peptide Synthesis*; Springer Verlag Heidelberg 1984) or with other suitable coupling reagents. Alternatively, the active esters may be isolated and then further reacted in a subsequent step. The Boc protecting group is then eliminated under acidic conditions. Thereafter, the deprotected amino group is acylated with activated carboxylic acid compounds, for example carboxylic acid halides or active esters. The latter are either produced in situ with suitable coupling reagents such as for example 4-(4,6-dimethoxy-1,3,5-triazin-2-yl)-4-methylmorpholinium chloride or peptide coupling reagents known from the literature, such as for example diisopropylcarbodiimide/N-hydroxybenzotriazole or are introduced as separately produced reactants.

Alternative Synthesis Scheme, Acylamino Acid Cyclohexylamide Compounds (VI):

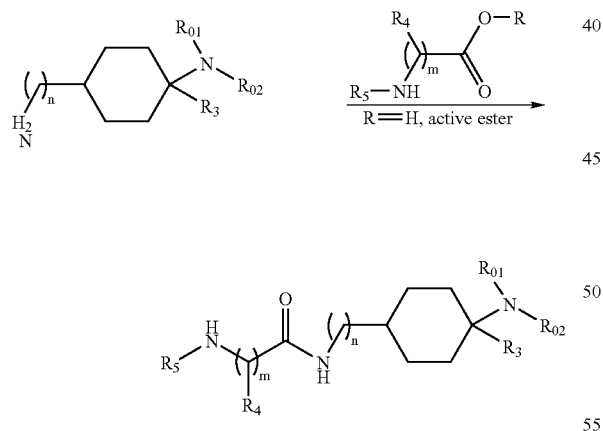

The 4-aminocyclohexyl(alkyl)amine intermediates (described in synthesis schemes I, III or VII) are acylated with amino acid compounds activated on the carboxyl terminus, which are commercially obtainable, these compounds being produced in situ using conventional peptide coupling methods known from the literature (Miklos Bodanszky, Agnes Bodanszky, *The Practice of Peptide Synthesis*; Springer Verlag Heidelberg 1984) or with other suitable coupling reagents. Alternatively, the active esters may be isolated and then further reacted in a subsequent step.

General Synthesis Scheme for the Production of Cyclohexylethylureas (VII):

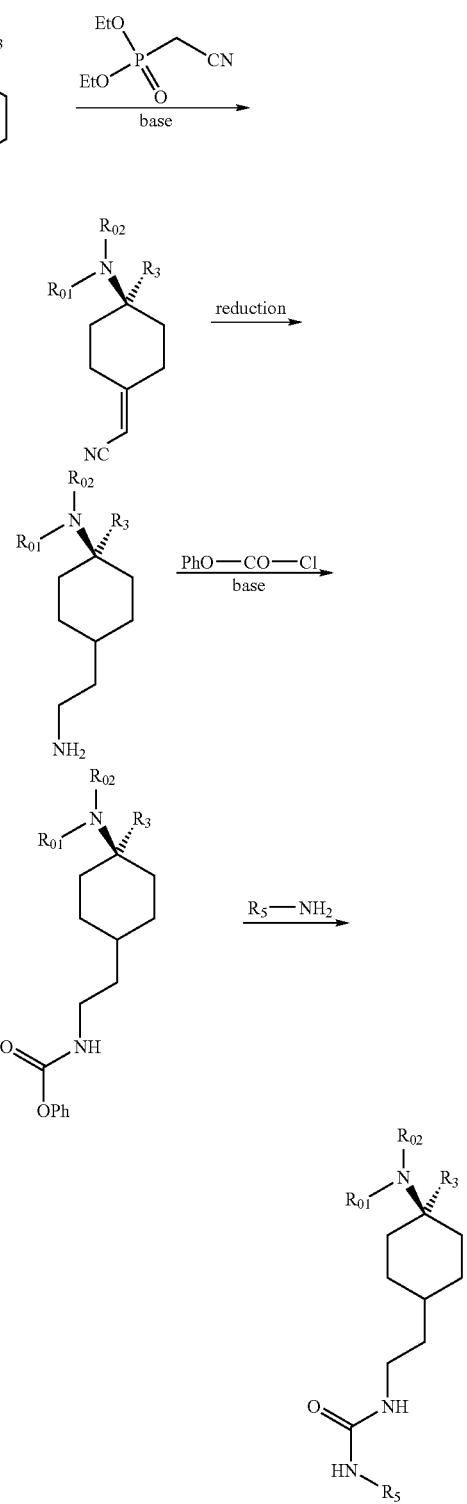

A 4-aminocyclohexanone (produced according to the literature as described in synthesis scheme I) is reacted, for example according to Horner, with cyanomethanephosphonic acid diethyl ester to yield the $\alpha,\beta$-unsaturated nitrile. The nitrile may be reduced either in two stages by conversion into the saturated nitrile, for example by catalytic hydrogenation with hydrogen on palladium/carbon and subsequent reduction to the amine, for example with sodium borohydride in the presence of cobalt or nickel chloride. Reduction to the saturated amine may, however, preferably be performed in a single stage by the use of, for example, sodium borohydride in the presence of cobalt or nickel chloride.

The primary amino group of the 4-aminoethylcyclohexylamines is reacted with activated carbonic acid compounds such as for example with chloroformic acid phenyl ester, chloroformic acid p-nitrophenyl ester or the like and a suitable base, for example pyridine or DMAP. The resulting intermediates, for example carbamic acid esters, are reacted with primary amines to yield the corresponding ureas.

Alternative Synthesis Scheme for the Production of Cyclohexylethylureas (VIII):

General Synthesis Scheme for the Production of Cyclohexylpropylureas (IX):

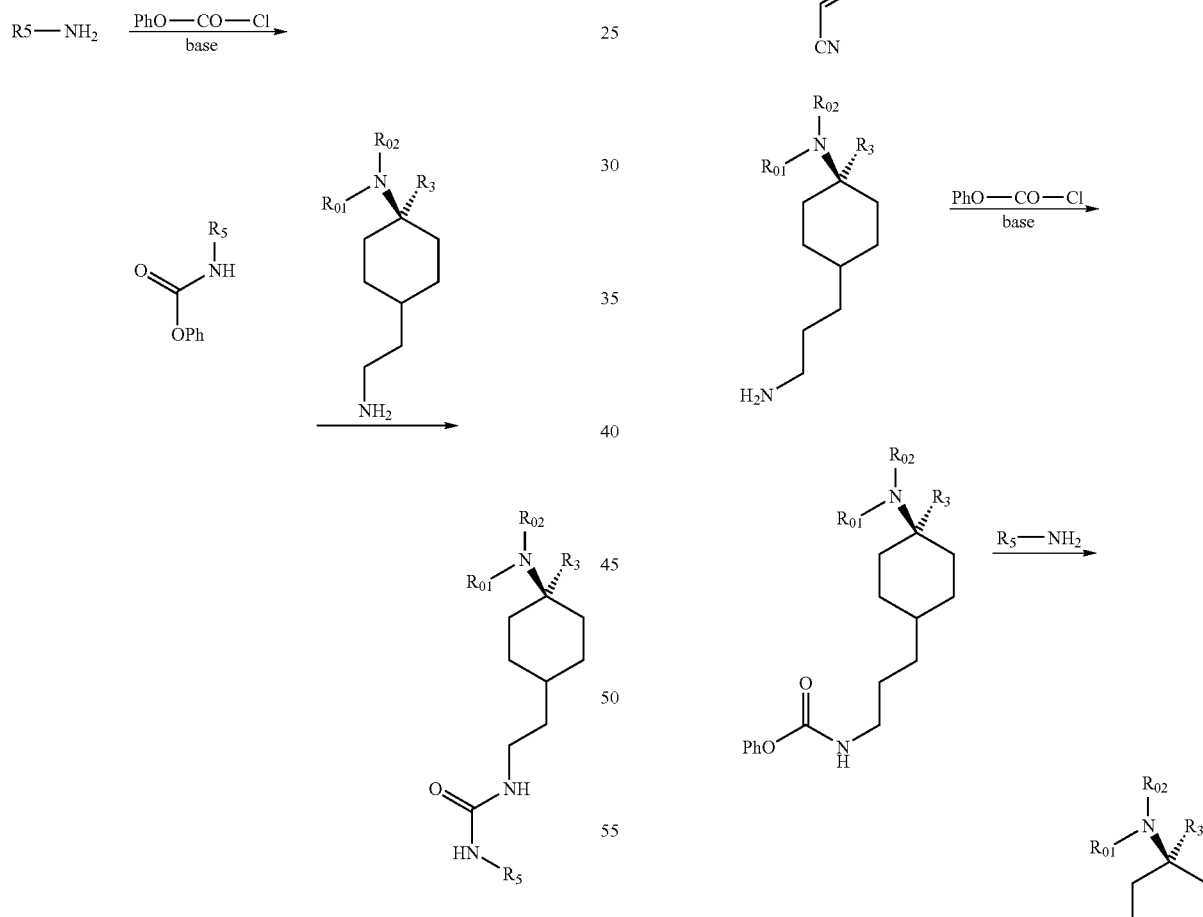

A primary amine is reacted with activated carbonic acid compounds, such as for example with chloroformic acid phenyl ester, chloroformic acid p-nitrophenyl ester or the like and a suitable base, for example pyridine or DMAP. The intermediates obtained, for example carbamic acid esters, are reacted with a 4-aminoethylcyclohexylamine (described in synthesis scheme VII) to yield the corresponding ureas.

A 4-aminocyclohexanecarbaldehyde (as described in synthesis scheme III) is reacted, for example according to Horner with cyanomethanephosphonic acid diethyl ester to yield the α,β-unsaturated nitrile. Reduction of the nitrile may be performed either in two stages by conversion into the saturated nitrile, for example by catalytic hydrogenation with hydrogen on palladium/carbon and subsequent reduction to the amine, for example with sodium borohydride in the presence of cobalt or nickel chloride. Reduction to the saturated amine may, however, preferably be performed in a single stage by the use of, for example, sodium borohydride in the presence of cobalt or nickel chloride.

The primary amino group of the 4-aminopropylcyclohexylamine is reacted with activated carbonic acid compounds such as for example with chloroformic acid phenyl ester, chloroformic acid p-nitrophenyl ester or the like and a suitable base, for example pyridine or DMAP. The intermediates obtained, for example carbamic acid esters, are reacted with primary amines to yield the corresponding ureas.

Alternative Synthesis Scheme for the Production of Cyclohexylpropylureas (X):

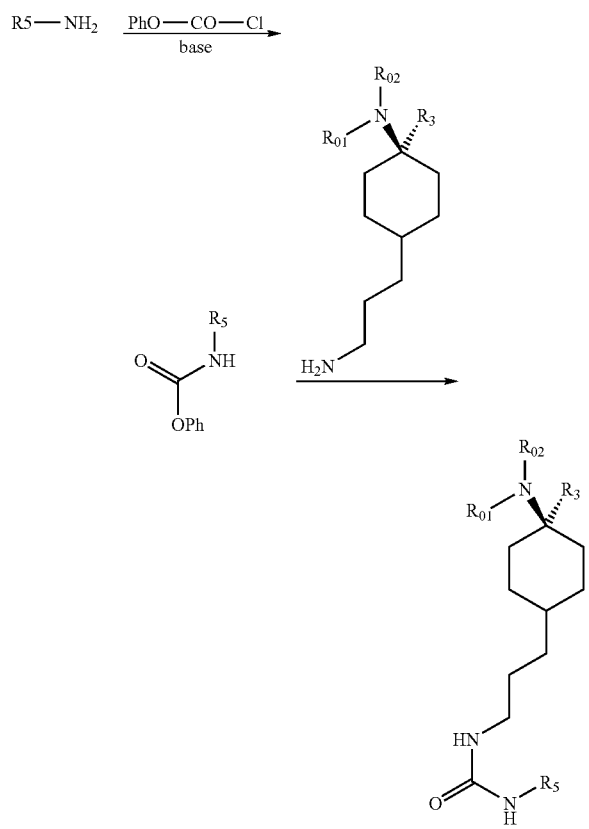

A primary amine is reacted with activated carbonic acid compounds, such as for example with chloroformic acid phenyl ester, chloroformic acid p-nitrophenyl ester or the like, and a suitable base, for example pyridine or DMAP. The resulting intermediates, for example carbamic acid esters, are reacted with a 4-aminopropylcyclohexylamine (described in synthesis scheme IX) to yield the corresponding ureas.

Alternative Synthesis Scheme for the Production of Cyclohexyl(alkyl)ureas Using Isocyanates (XI):

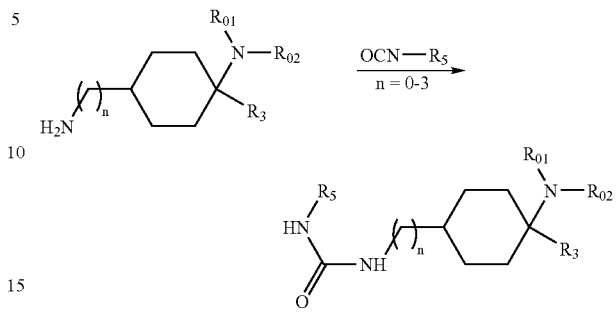

The above-described cyclohexyl(alkyl)amines may also be carbamoylated in a reaction step with isocyanates. The isocyanates are either commercially obtainable or may be produced using methods described in the literature, for example from phosgene or phosgene equivalents and primary amines, or rearrangement from the corresponding carboxylic acid compounds which are one carbon atom longer (for example from carboxylic acid azides by Curtius degradation).

General Synthesis Scheme for the Production of Cyclohexyl(alkyl)thioureas Using Isothiocyanates (XII):

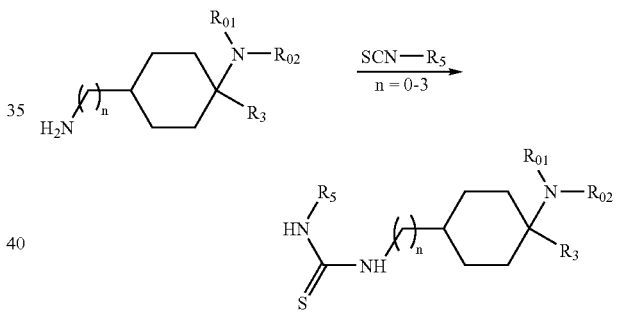

The above-described cyclohexyl(alkyl)amines may also be reacted in a reaction step with isothiocyanates. The isothiocyanates are either commercially obtainable or may be produced using methods known from the literature, for example from thiophosgene or thiophosgene equivalents and primary amines.

EXAMPLES

The following Examples illustrate the invention in further detail without limiting its scope. The yields of the compounds produced are not optimized. All temperatures are uncorrected.

In the examples, the term "Ether" means diethyl ether, "EE" means ethyl acetate and "DCM" means dichloromethane. "Equivalents" means quantity equivalents, "m.p." means melting point or melting range, "RT" means room temperature, "vol. %" means percent by volume, "m %" means mass percent and "M" is a concentration in moles/liter.

Silica gel 60 (0.040-0.063 mm) from E. Merck, Darmstadt, was used as the stationary phase for the column chromatography. Thin-layer chromatography was performed with pre-coated silica gel 60 F 254 HPTLC plates from E. Merck, Darmstadt. The mobile solvent mixture ratios for chromatographic investigations are always stated by volume/volume.

(3-Phenylpropyl)carbamic acid phenyl ester

Chloroformic acid phenyl ester (3.29 g, 21.0 mmole) and pyridine (1.74 g, 22.0 mmole) were added to a solution of 3-phenylpropylamine (2.7 g, 20.0 mmole) in $CH_2Cl_2$ and stirred for 24 h at room temperature. Working up was performed by extracting the batch successively with $H_2O$, 1M HCl and 1M NaOH. The organic phase was dried with $Na_2SO_4$ and evaporated. The product was obtained as a colorless solid (m.p. 55-56° C.) in a yield of 4.11 g (81%) by recrystallisation from ethyl acetate/hexane (1:1).

1-(4-Dimethylamino-4-phenylcyclohexyl)-3-(3-phenylpropyl)urea

4-Dimethylamino-4-phenyl-cyclohexylamine (more nonpolar diastereomer) (218 mg, 1.0 mmole) was added to a solution of (3-phenylpropyl)carbamic acid phenyl ester (255 mg, 1.0 mmole) in dioxane and refluxed for 12 h. Working up was performed by removing the dioxane by distillation and combining the residue with water. The batch was adjusted to pH 11 with 5M NaOH and extracted with ethyl acetate. The organic phase was dried with $Na_2SO_4$ and evaporated. The more nonpolar product was obtained as a colorless oil in a yield of 200 mg (53%).

4-Dimethylamino-4-phenyl-cyclohexylamine (more polar diastereomer) (218 mg, 1.0 mmole) was added to a solution of (3-phenylpropyl)carbamic acid phenyl ester (255 mg, 1.0 mmole) in dioxane and refluxed for 12 h. Working up was performed by removing the dioxane by distillation and combining the residue with water. The batch was adjusted to pH 11 with 5M NaOH and extracted with ethyl acetate. The organic phase was dried with $Na_2SO_4$ and evaporated. The more polar product was obtained as a colorless oil in a yield of 379 mg (100%).

Examples 1 and 2

1-(4-Dimethylamino-4-phenylcyclohexyl)-3-(3-phenylpropyl)urea hydrochloride

In order to produce the hydrochloride (Example 1), the more nonpolar urea (200 mg, 0.53 mmole) was dissolved in ethyl methyl ketone and combined with trimethylchlorosilane (101 µl, 0.8 mmole). The resulting solid was removed by suction filtration and dried. In this manner, the product was obtained as a colorless solid (m.p. 33-35° C.) in a yield of 219 mg (100%).

In order to produce the-hydrochloride, (Example 2), the more polar urea (379 mg, 1.0 mmole) was dissolved in ethyl methyl ketone (5 ml) and combined with trimethylchlorosilane (190 µl, 1.5 mmole). The resulting solid was removed by suction filtration and dried. In this manner, the product was obtained as a colorless solid in a yield of 416 mg (100%). This compound was hygroscopic.

[2-(1H-Indol-3-yl)ethyl]carbamic acid phenyl ester

Chloroformic acid phenyl ester (3.29 g, 21.0 mmole) and pyridine (1.74 g, 22.0 mmole) were added to a solution of tryptamine (3.2 g, 20.0 mmole) in $CH_2Cl_2$ and stirred for 24 h at room temperature. Working up was performed by extracting the batch successively with water, with 1M HCl and with 1M NaOH. The organic phase was dried with $Na_2SO_4$ and evaporated. The product was obtained as a colorless solid (m.p. 44-46° C.) in a yield of 5.58 g (100%).

1-(4-Dimethylamino-4-phenylcyclohexyl)-3-[2-(1H-indol-3-yl)ethyl]urea

4-Dimethylamino-4-phenyl-cyclohexylamine (more nonpolar diastereomer) (218 mg, 1.0 mmole) was added to a solution of [2-(1H-indol-3-yl)ethyl]carbamic acid phenyl ester (280 mg, 1.0 mmole) in dioxane and refluxed for 12 h. Working up was performed by removing the dioxane by distillation and combining the residue with water. The batch was adjusted to pH 11 with 5M NaOH and extracted with ethyl acetate. The organic phase was dried with $Na_2SO_4$ and evaporated. The product was obtained as a colorless oil in a yield of 404 mg (100%).

4-Dimethylamino-4-phenyl-cyclohexylamine (more polar diastereomer) (218 mg, 1.0 mmole) was added to a solution of [2-(1H-indol-3-yl)ethyl]carbamic acid phenyl ester (280 mg, 1.0 mmole) in dioxane and refluxed for 12 h. Working up was performed by removing the dioxane by distillation and combining the residue with water. The batch was adjusted to pH 11 with 5M NaOH and extracted with ethyl acetate. The organic phase was dried with $Na_2SO_4$ and evaporated. The product was obtained as a colorless oil in a yield of 404 mg (100%).

Examples 3 and 4

1-(4-Dimethylamino-4-phenylcyclohexyl)-3-[2-(1H-indol-3-yl)ethyl]urea-hydrochloride In order to produce the hydrochloride (Example 3), the more nonpolar urea (404 mg, 1.0 mmole) was dissolved in ethyl methyl ketone and combined with trimethylchlorosilane (190 µl, 1.5 mmole). The resulting solid was removed by suction filtration and dried. The hydrochloride (Example 3), was obtained in this manner as a colorless solid (m.p. 99-101° C.) in a yield of 440 mg (100%).

In order to produce the hydrochloride (Example 4), the more polar urea (404 mg, 1.0 mmole) was dissolved in ethyl methyl ketone and combined with trimethylchlorosilane (190 µl, 1.5 mmole). The resulting solid was removed by suction filtration and dried. The hydrochloride (Example 4), was obtained in this manner as a colorless solid (m.p. 185-187° C.) in a yield of 440 mg (100%).

[(4-Dimethylamino-4-phenylcyclohexylcarbamoyl) methyl]carbamic acid tert.-butyl ester N-tert.-Butyloxycarbonyl-glycine-N-hydroxysuccinimide ester (272 mg, 1.0 mmole) was added to a solution of 4-dimethylamino-4-phenyl-cyclohexylamine (more nonpolar diastereomer) (218 mg, 1.0 mmole) in acetonitrile and stirred for 24 h at room temperature. Working up was performed by removing the acetonitrile by distillation in a rotary evaporator. The batch was re-dissolved with water, adjusted to pH 11 with 5M NaOH and extracted with ethyl acetate. The organic phase was dried with $Na_2SO_4$ and evaporated. The product was obtained as a colorless solid in a yield of 370 mg (99%).

N-tert.-Butyloxycarbonyl-glycine-N-hydroxysuccinimide ester (1.05 g, 3.85 mmole) was added to a solution of 4-dimethylamino-4-phenyl-cyclohexylamine (more polar diastereomer) (840 mg, 3.85 mmole) in acetonitrile and stirred for 24 h at room temperature. Working up was performed by removing the acetonitrile by distillation. The batch was re-dissolved with water, adjusted to pH 11 with 5M NaOH and extracted with ethyl acetate. The organic phase was dried with $Na_2SO_4$ and evaporated. The product was obtained as a colorless solid in a yield of 1.39 g (97%).

2-Amino-N-(4-dimethylamino-4-phenylcyclohexyl) acetamide hydrochloride

In order to produce the more nonpolar hydrochloride with simultaneous elimination of the Boc group, the more nonpolar amide (370 mg, 1.0 mmole) was dissolved in EtOH and combined with 3.3M ethanolic HCl (763 µl, 2.5 mmole). The resulting solid was filtered out and dried. The hydrochloride of the more nonpolar amine was obtained as a colorless solid (m.p. 162-164° C.) in a yield of 360 mg (100%).

In order to produce the more polar hydrochloride with simultaneous elimination of the Boc group, the more polar amide (1.39 mg, 3.7 mmole) was dissolved in EtOH and combined with 3.3M ethanolic HCl (2.82 µl, 9.3 mmole). The resulting solid was filtered out and dried. The hydrochloride of the more polar amine was obtained as a colorless solid in a yield of 1.35 g (100%).

N-[(4-Dimethylamino-4-phenylcyclohexylcarbamoyl)methyl]-3-(1H-indol-3-yl)butyramide The more nonpolar diastereomer of 2-amino-N-(4-dimethylamino-4-phenylcyclohexyl)acetamide (276 mg, 1.0 mmole) and 4-(4,6-dimethoxy-1,3,5-triazin-2-yl)-4-methylmorpholinium chloride (415 mg, 1.5 mmole) were added to a solution of indol-3-yl-butyric acid (203 mg, 1.0 mmole) in MeOH and stirred for 24 h at room temperature. Working up was performed by removing MeOH by distillation. The batch was re-dissolved with water, adjusted to pH 11 with 5M NaOH and extracted with ethyl acetate. The organic phase was dried with $Na_2SO_4$ and evaporated. The more nonpolar amide was obtained as a colorless oil in a yield of 450 mg (98%).

The more polar diastereomer of 2-amino-N-(4-dimethylamino-4-phenylcyclohexyl)-acetamide (159 mg, 0.57 mmole) and 4-(4,6-dimethoxy-1,3,5-triazin-2-yl)-4-methylmorpholinium chloride (239 mg, 0.86 mmole) were added to a solution of indol-3-yl-butyric acid (117 mg, 0.57 mmole) in MeOH and stirred for 24 h at room temperature. Working up was performed by removing MeOH by distillation. The batch was re-dissolved with water, adjusted to pH 11 with 5M NaOH and extracted with ethyl acetate. The organic phase was dried with $Na_2SO_4$ and evaporated. The more polar amide was obtained as a colorless oil in a yield of 265 mg (100%).

Examples 5 and 6

N-[(4-Dimethylamino-4-phenylcyclohexylcarbamoyl)methyl]-3-(1H-indol-3-yl)butyramide hydrochloride In order to produce the hydrochloride (Example 5), the more nonpolar diastereomer of N-[(4-dimethylamino-4-phenylcyclohexylcarbamoyl)methyl]-3-(1H-indol-3-yl)butyramide (450 mg, 0.98 mmole) was dissolved in ethyl methyl ketone and combined with trimethylchlorosilane (190 µl, 1.5 mmole). The resulting solid was filtered out and dried. The hydrochloride (Example 5) was obtained as a colorless solid (m.p. 134-136° C.) in a yield of 300 mg (60%).

In order to produce the hydrochloride (Example 6), the more polar diastereomer of N-[(4-dimethylamino-4-phenylcyclohexylcarbamoyl)methyl]-3-(1H-indol-3-yl)butyramide (265 mg, 0.57 mmole) was dissolved in ethyl methyl ketone and combined with trimethylchlorosilane (108 µl, 0.86 mmole). The resulting solid was filtered out and dried. The hydrochloride (Example 6) was obtained as a colorless solid (m.p. 148-150° C.) in a yield of 225 mg (79%).

5-(1H-Indol-3-yl)pentanoic acid [(4-dimethylamino-4-phenylcyclohexylcarbamoyl)-methyl]amide The more nonpolar diastereomer of 2-amino-N-(4-dimethylamino-4-phenylcyclohexyl)-acetamide (276 mg, 1.0 mmole) and 4-(4,6-dimethoxy-1,3,5-triazin-2-yl)-4-methylmorpholinium chloride (415 mg, 1.5 mmole) were added to a solution of indol-3-yl-pentanoic acid (217 mg, 1.0 mmole) in MeOH and stirred for 24 h at room temperature. Working up was performed by removing MeOH by distillation. The batch was re-dissolved with water, adjusted to pH 11 with 5M NaOH and extracted with ethyl acetate. The organic phase was dried with $Na_2SO_4$ and evaporated. The more nonpolar amide was obtained as a colorless oil in a yield of 474 mg (100%).

The more polar diastereomer of 2-amino-N-(4-dimethylamino-4-phenylcyclohexyl)-acetamide (159 mg, 0.57 mmole) and 4-(4,6-dimethoxy-1,3,5-triazin-2-yl)-4-methylmorpholinium chloride (239 mg, 0.86 mmole) were added to a solution of indol-3-yl-pentanoic acid (125 mg, 0.57 mmole) in MeOH and stirred for 24 h at room temperature. Working up was performed by removing MeOH by distillation. The batch was re-dissolved with water, adjusted to pH 11 with 5M NaOH and extracted with ethyl acetate. The organic phase was dried with $Na_2SO_4$ and evaporated. The more polar amide was obtained as a colorless oil in a yield of 273 mg (100%).

Examples 7 and 8

5-(1H-Indol-3-yl)-pentanoic acid [(4-dimethylamino-4-phenylcyclohexylcarbamoyl)methyl]amide hydrochloride In order to produce Example 7, the more nonpolar diastereomer of 5-(1H-indol-3-yl)pentanoic acid [(4-dimethylamino-4-phenylcyclohexylcarbamoyl)methyl]amide (474 mg, 1.0 mmole) was dissolved in ethyl methyl ketone and combined with trimethylchlorosilane (190 µl, 1.5 mmole). The resulting solid was filtered out and dried. The hydrochloride (Example 7) was obtained as a pink solid (m.p. 45-47° C.) in a yield of 440 mg (86%).

In order to produce Example 8, the more polar diastereomer of 5-(1H-indol-3-yl)pentanoic acid [(4-dimethylamino-4-phenylcyclohexylcarbamoyl)-methyl]amide (273 mg, 0.57 mmole) was dissolved in ethyl methyl ketone and combined with trimethylchlorosilane (108 µl, 0.86 mmole). The resulting solid was filtered out and dried. The hydrochloride (Example 8), was obtained as a pink solid (m.p. 54-56° C.) in a yield of 200 mg (68%).

6-(1H-Indol-3-yl)hexanoic acid [(4-dimethylamino-4-phenylcyclohexylcarbamoyl)methyl]amide The more nonpolar diastereomer of 2-amino-N-(4-dimethylamino-4-phenylcyclohexyl)-acetamide (276 mg, 1.0 mmole) and 4-(4,6-dimethoxy-1,3,5-triazin-2-yl)-4-methylmorpholinium chloride (415 mg, 1.5 mmole) were added to a solution of indol-3-yl-hexanoic acid (231 mg, 1.0 mmole) in MeOH and stirred for 24 h at room temperature. Working up was performed by removing MeOH by distillation. The batch was re-dissolved with water, adjusted to pH 11 with 5M NaOH and extracted with ethyl acetate, The organic phase was dried with $Na_2SO_4$ and evaporated. The more nonpolar amide was obtained as a colorless oil in a yield of 525 mg (100%).

The more polar diastereomer of 2-amino-N-(4-dimethylamino-4-phenylcyclohexyl)-acetamide (159 mg, 0.57 mmole) and 4-(4,6-dimethoxy-1,3,5-triazin-2-yl)-4-methylmorpholinium chloride (239 mg, 0.86 mmole) were added to a solution of indol-3-yl-hexanoic acid (133 mg, 0.57 mmole) in MeOH and stirred for 24 h at room temperature. Working up was performed by removing MeOH by distillation. The batch was re-dissolved with water, adjusted to pH 11 with 5M NaOH and extracted with ethyl acetate. The organic phase was dried with $Na_2SO_4$ and evaporated. The more polar amide was obtained as a colorless oil in a yield of 281 mg (100%).

Examples 9 and 10

6-(1H-Indol-3-yl)hexanoic acid [(4-dimethylamino-4-phenylcyclohexylcarbamoyl)-methyl]-amide hydrochloride In order to produce the hydrochloride (Example 9), the more nonpolar diastereomer of 6-(1H-indol-3-yl)hexanoic acid [(4-dimethylamino-4-phenylcyclohexylcarbamoyl)-methyl]amide (525 mg, 1.0 mmole) was dissolved in ethyl methyl ketone and combined with trimethylchlorosilane (190 µl, 1.5 mmole). The resulting solid was filtered out and dried. The hydrochloride (Example 9), was obtained as a pink solid (m.p. 32-34° C.) in a yield of 402 mg (82%).

In order to produce the hydrochloride (Example 10), the more polar diastereomer of 6-(1H-indol-3-yl)hexanoic acid [(4-dimethylamino-4-phenylcyclohexylcarbamoyl)-methyl] amide (281 mg, 0.57 mmole) was dissolved in ethyl methyl ketone and combined with trimethylchlorosilane (108 µl, 0.86 mmole). The resulting solid was filtered out and dried. The hydrochloride (Example 10) was obtained as a pink solid (m.p. 31-33° C.) in a yield of 300 mg (99%).

N-[(4-Dimethylamino-4-phenylcyclohexylcarbamoyl)methyl]-3-(1H-indol-3-yl)propionamide The more nonpolar diastereomer of 2-amino-N-(4-dimethylamino-4-phenylcyclohexyl)-acetamide (276 mg, 1.0 mmole) and 4-(4,6-dimethoxy-1,3,5-triazin-2-yl)-4-methylmorpholinium chloride (415 mg, 1.5 mmole) were added to a solution of indol-3-yl-propionic acid (189 mg, 1.0 mmole) in MeOH and stirred for 24 h at room temperature. Working up was performed by removing MeOH by distillation. The batch was re-dissolved with water, adjusted to pH 11 with 5M NaOH and extracted with ethyl acetate. The organic phase was dried with $Na_2SO_4$ and evaporated. The more nonpolar amide was obtained as a colorless oil in a yield of 446 mg (100%).

The more polar diastereomer of 2-amino-N-(4-dimethylamino-4-phenylcyclohexyl)-acetamide (159 mg, 0.57 mmole) and 4-(4,6-dimethoxy-1,3,5-triazin-2-yl)-4-methylmorpholinium chloride (239 mg, 0.86 mmole) were added to a solution of indol-3-yl-propionic acid (109 mg, 0.57 mmole) in MeOH and stirred for 24 h at room temperature. Working up was performed by removing MeOH by distillation. The batch was re-dissolved with water, adjusted to pH 11 with 5M NaOH and extracted with ethyl acetate. The organic phase was dried with $Na_2SO_4$ and evaporated. The more polar amide was obtained as a colorless oil in a yield of 257 mg (100%).

Examples 11 and 12

N-[(4-Dimethylamino-4-phenylcyclohexylcarbamoyl)methyl]-3-(1H-indol-3-yl)propionamide hydrochloride In order to produce the hydrochloride (Example 11), the more nonpolar diastereomer of N-[(4-dimethylamino-4-phenylcyclohexylcarbamoyl)methyl]-3-(1H-indol-3-yl)propionamide (446 mg, 1.0 mmole) was dissolved in ethyl methyl ketone and combined with trimethylchlorosilane (190 µl, 1.5 mmole). The resulting solid was filtered out and dried. Example 11 was obtained as a colorless solid (m.p. of 143-145° C.) in a yield of 370 mg (77%).

In order to produce the hydrochloride (Example 12), the more polar diastereomer of N-[(4-dimethylamino-4-phenylcyclohexylcarbamoyl)methyl]-3-(1H-indol-3-yl)propionamide (257 mg, 0.57 mmole) was dissolved in ethyl methyl ketone and combined with trimethylchlorosilane (108 µl, 0.86 mmole). The resulting solid was filtered out and dried. Example 12 was obtained as a colorless solid (m.p. 135-137° C.) in a yield of 220 mg (79%).

N-(4-Dimethylamino-4-phenylcyclohexyl)-2-(2-1H-indol-3-ylacetylamino)-propionamide The more nonpolar diastereomer of (4-dimethylamino-4-phenylcyclohexyl)amine (109 mg, 0.5 mmole) and 4-(4,6-dimethoxy-1,3,5-triazin-2-yl)-4-methylmorpholinium chloride (208 mg, 0.75 mmole) were added to a solution of N-(indolyl-3-yl-acetyl)-L-alanine (123 mg, 0.5 mmole) in MeOH and stirred for 24 h at room temperature. Working up was performed by removing MeOH by distillation. The residue was re-dissolved with water, adjusted to pH 11 with 5M NaOH and extracted with ethyl acetate. The organic phase was dried with $Na_2SO_4$ and evaporated. The more nonpolar amide was obtained as a colorless oil in a yield of 110 mg (49%).

The more polar diastereomer of (4-dimethylamino-4-phenyl-cyclohexyl)amine (143 mg, 0.66 mmole) and 4-(4,6-dimethoxy-1,3,5-triazin-2-yl)-4-methylmorpholinium chloride (272 mg, 0.98 mmole) were added to a solution of N-(indolyl-3-yl-acetyl)-L-alanine (161 mg, 0.66 mmole) in MeOH and stirred for 24 h at room temperature. Working up was performed by removing MeOH by distillation. The residue was re-dissolved with water, adjusted to pH 11 with 5M NaOH and extracted with ethyl acetate. The organic phase was dried with $Na_2SO_4$ and evaporated. The more polar amide was obtained as a colorless oil in a yield of 297 mg (100%).

Examples 13 and 14

N-(4-Dimethylamino-4-phenylcyclohexyl)-2-(2-1H-indol-3-ylacetylamino)-propionamide hydrochloride In order to produce the hydrochloride (Example 13), the more nonpolar diastereomer of N-(4-dimethylamino-4-phenylcyclohexyl)-2-(2-1H-indol-3-ylacetylamino)propionamide (110 mg, 0.25 mmole) was dissolved in ethyl methyl ketone and combined with trimethylchlorosilane (48 µl, 0.38 mmole). The resulting solid was filtered out and dried. Example 13 was obtained as a colorless solid (m.p. 98-100° C.) in a yield of 119 mg (100%).

In order to produce the hydrochloride (Example 14), the more polar diasteromer of N-(4-dimethylamino-4-phenyl-cyclohexyl)-2-(2-1H-indol-3-ylacetylamino)propionamide (297 mg, 0.66 mmole) was dissolved in ethyl methyl ketone and combined with trimethylchlorosilane (125 µl, 0.99 mmole). The resulting solid was filtered out and dried. Example 14 was obtained as a colorless solid (m.p. 30-32° C.) in a yield of 200 mg (63%).

2-(2-1H-Indol-3-ylacetylamino)-4-methylpentanoic acid (4-dimethylamino-4-phenylcyclohexyl)amide The more nonpolar diastereomer of (4-dimethylamino-4-phenyl-cyclohexyl)amine (109 mg, 0.5 mmole) and 4-(4,6-dimethoxy-1,3,5-triazin-2-yl)-4-methylmorpholinium chloride (208 mg, 0.75 mmole) were added to a solution of N-(3-indolylacetyl)-L-leucine (144 mg, 0.5 mmole) in MeOH and stirred for 24 h at room temperature. Working up was performed by removing MeOH by distillation. The residue was re-dissolved with water, adjusted to pH 11 with 5M NaOH and extracted with ethyl acetate. The organic phase was dried with $Na_2SO_4$ and evaporated. The product was obtained as a colorless oil in a yield of 115 mg (47%).

The more polar diastereomer of (4-dimethylamino-4-phenyl-cyclohexyl)amine (143 mg, 0.66 mmole) and 4-(4,6-dimethoxy-1,3,5-triazin-2-yl)-4-methylmorpholinium chloride (272 mg, 0.98 mmole) were added to a solution of N-(3-indolylacetyl)-L-leucine (189 mg, 0.66 mmole) in MeOH and stirred for 24 h at room temperature. Working up was performed by removing MeOH by distillation. The residue was re-dissolved with water, adjusted to pH 11 with 5M NaOH and extracted with ethyl acetate. The organic phase was dried with $Na_2SO_4$ and then evaporated. The product was obtained as a colorless oil in a yield of 320 mg (100%).

Examples 15 and 16

2-(2-1H-Indol-3-ylacetylamino)-4-methylpentanoic acid (4-dimethylamino-4-phenylcyclohexyl)amide hydrochloride In order to produce the hydrochloride (Example 15), the more nonpolar compound of 2-(2-1H-indol-3-ylacetylamino)-4-methylpentanoic acid-(4-dimethylamino-4-phenylcyclohexyl)amide (115 mg, 0.24 mmole) was dissolved in ethyl methyl ketone and combined with trimethylchlorosilane (48 µl, 0.38 mmole). The resulting solid was filtered out and dried. Example 15 was obtained as a colorless solid (m.p. 118-120° C.) in a yield of 123 mg (100%).

In order to produce the hydrochloride (Example 16), the more polar compound of 2-(2-1H-indol-3-ylacetylamino)-4-methylpentanoic acid-(4-dimethylamino-4-phenylcyclohexyl)amide (320 mg, 0.66 mmole) was dissolved in ethyl methyl ketone and combined with trimethylchlorosilane (125 µl, 0.99 mmole). The resulting solid was filtered out and dried. Example 16 was obtained as a colorless solid (m.p. 174-176° C.) in a yield of 170 mg (50%).

1-(4-Dimethylamino-4-phenylcyclohexyl)-3-[2-(1H-indol-3-yl)ethyl]-thiourea 2-(1H-Indol-3-yl)-ethylamine (tryptamine; 320 mg, 2 mmole) was dissolved in dry chloroform (10 ml) and combined with triethylamine (555 µl, 4 mmole). Thiophosgene (153 µl, 2 mmole) was added to this mixture. After a reaction time of 16 h, N,N-dimethyl-1-phenyl-cyclohexane-1,4-diamine was added and stirring continued for a further 16 h at RT. Working up was performed by extracting the batch with saturated $NaHCO_3$ solution (3×20 ml). The organic phase was dried with $Na_2SO_4$ and evaporated. The product was a mixture of two diastereoisomers and could be purified by column chromatography [silica gel 60 (50 g); methanol (500 ml)]. The more polar diastereoisomer of 1-(4-dimethylamino-4-phenyl-cyclohexyl)-3-[2-(1H-indol-3-yl)-ethyl]-thiourea was obtained as a colorless foam in a yield of 185 mg (22%). The more nonpolar diastereoisomer of 1-(4-dimethylamino-4-phenyl-cyclohexyl)-3-[2-(1H-indol-3-yl)-ethyl]-thiourea was obtained as a colorless foam in a yield of 433 mg (52%).

[2-(1H-indol-3-yl)-1-methylethyl]carbamic acid phenyl ester

Chloroformic acid phenyl ester (760 µl, 6.03 mmole) and pyridine (510 µl, 6.31 mmole) were added to a solution of 2-(1H-indol-3-yl)-1-methyl-ethylamine (1.0 g, 5.74 mmole) in abs. DCM (20 ml). Stirring was then performed for 24 h at RT. Working up was performed by extracting the batch with water (2×20 ml), with 1M HCl (2×20 ml) and with 1M NaOH (2×20 ml). The organic phase was dried with $Na_2SO_4$ and evaporated. [2-(1H-Indol-3-yl)-1-methylethyl]carbamic acid phenyl ester was obtained as a colorless solid in a yield of 1.35 g (80%).

1-(4-Dimethylamino-4-phenylcyclohexyl)-3-[2-(1H-indol-3-yl)-1-methylethyl]urea

The more nonpolar diastereoisomer of N,N-dimethyl-1-phenyl-cyclohexane-1,4-diamine (109 mg, 0.5 mmole) was added to a solution of [2-(1H-indol-3-yl)-1-methyl-ethyl]-carbamic acid phenyl ester (147 mg, 0.5 mmole) in dioxane (10 ml). The batch was then refluxed for 6 h. Working up was performed by removing dioxane by distillation and diluting the batch with water (10 ml). The batch was adjusted to pH 11 with 5M NaOH and extracted with EE (3×20 ml). The organic phase was dried with $Na_2SO_4$ and evaporated. The more nonpolar diastereoisomer of 1-(4-dimethylamino-4-phenylcyclohexyl)-3-[2-(1H-indol-3-yl)-1-methylethyl]urea was obtained after chromatography on silica gel with methanol as a colorless oil in a yield of 125 mg (60%).

The more polar diastereoisomer of N,N-dimethyl-1-phenyl-cyclohexane-1,4-diamine (109 mg, 0.5 mmole) was added to a solution of [2-(1H-indol-3-yl)-1-methyl-ethyl]-carbamic acid phenyl ester (147 mg, 0.5 mmole) in dioxane (10 ml). The batch was then refluxed for 6 h. Working up was performed by removing dioxane by distillation and diluting the batch with water (10 ml). The batch was adjusted to pH 11 with 5M NaOH and extracted with EE (3×20 ml). The organic phase was dried with $Na_2SO_4$ and evaporated. The more polar diastereoisomer of 1-(4-dimethylamino-4-phenylcyclohexyl)-3-[2-(1H-indol-3-yl)-1-methylethyl]urea was obtained after chromatography on silica gel with methanol as a colorless oil in a yield of 100 mg (48%).

Examples 17 and 18

1-(4-Dimethylamino-4-phenylcyclohexyl)-3-[2-(1H-indol-3-yl)-1-methyl-ethyl]urea hydrochloride In order to produce 1-(4-dimethylamino-4-phenylcyclohexyl)-3-[2-(1H-indol-3-yl)-1-methylethyl]urea hydrochloride (Example 17), the more nonpolar diastereoisomer of 1-(4-dimethylamino-4-phenylcyclohexyl)-3-[2-1H-indol-3-yl)-1-methylethyl]urea (125 mg, 0.3 mmole) was dissolved in ethyl methyl ketone (3 ml) and combined with trimethylchlorosilane (57 µl, 0.45 mmole). The resulting solid was filtered out and dried. The hydrochloride of the more nonpolar diastereoisomer of 1-(4-dimethylamino-4-phenylcyclohexyl)-3-[2-(1H-indol-3-yl)-1-methyl-ethyl]urea was obtained in this manner as a colorless solid with a melting point of 154-156° C. in a yield of 135 mg (100%).

In order to produce the hydrochloride (Example 18), the more polar diastereoisomer of 1-(4-dimethylamino-4-phenylcyclohexyl)-3-[2-(1H-indol-3-yl)-1-methyl-ethyl]urea (100 mg, 0.24 mmole) was dissolved in ethyl methyl ketone (3 ml) and combined with trimethylchlorosilane (46 µl, 0.36 mmole). The resulting solid was filtered out and dried. The hydrochloride of the more polar diastereoisomer of 1-(4-dimethylamino-4-phenylcyclohexyl)-3-[2-(1H-indol-3-yl)-1-methyl-ethyl]urea was obtained in this manner as a colorless solid with a melting point of 175-177° C. in a yield of 108 mg (100%).

[2-(5-fluoro-1H-indol-3-yl)ethyl]carbamic acid phenyl ester

Chloroformic acid phenyl ester (310 µl, 2.45 mmole) and pyridine (415 µl, 5.13 mmole) were added to a solution of 2-(5-fluoro-1H-indol-3-yl)-ethylamine (0.5 g, 2.33 mmole) in abs. DCM (10 ml). Stirring was then performed for 24 h at RT. Working up was performed by extracting the batch with water (2×20 ml), with 1M HCl (2×20 ml) and with 1M NaOH (2×20 ml). The organic phase was dried with $Na_2SO_4$ and evaporated. [2-(5-Fluoro-1H-indol-3-yl)-ethyl]-carbamic acid phenyl ester was obtained as a colorless solid in a yield of 0.69 g (100%).

1-(4-Dimethylamino-4-phenylcyclohexyl)-3-[2-(5-fluoro-1H-indol-3-yl)ethyl]urea The more nonpolar diastereoisomer of 4-dimethylamino-4-phenyl-cyclohexylamine (218 mg, 1.0 mmole) was added to a solution of [2-(5-fluoro-1H-indol-3-yl)-ethyl]-carbamic acid phenyl ester (298 mg, 1.0 mmole) in dioxane (20 ml). The batch was then refluxed for 8 h. Working up was performed by removing dioxane by distillation and diluting the batch with water (10 ml). The batch was adjusted to pH 11 with 5M NaOH and extracted with EE (3×20 ml). The organic phase was dried with $Na_2SO_4$ and evaporated. The more nonpolar diastereoisomer of 1-(4-dimethylamino-4-phenylcyclohexyl)-3-[2-(5-fluoro-1H-indol-3-yl)ethyl]urea was obtained after chromatography on silica gel with methanol as a colorless oil in a yield of 140 mg (33%).

The more polar diastereoisomer of 4-dimethylamino-4-phenyl-cyclohexylamine (271 mg, 1.24 mmole) was added to a solution of [2-(5-fluoro-1H-indol-3-yl)-ethyl]-carbamic acid phenyl ester (370 mg, 1.24 mmole) in dioxane (20 ml). The batch was then refluxed for 8 h. Working up was performed by removing dioxane by distillation and diluting the batch with water (10 ml). The batch was adjusted to pH 11 with 5M NaOH and extracted with EE (3×20 ml). The organic phase was dried with $Na_2SO_4$ and evaporated. The more polar diastereoisomer of 1-(4-dimethylamino-4-phenylcyclohexyl)-3-[2-(5-fluoro-1H-indol-3-yl)ethyl]urea was obtained after chromatography on silica gel with methanol as a colorless oil in a yield of 267 mg (51%).

Examples 19 and 20

1-(4-Dimethylamino-4-phenylcyclohexyl)-3-[2-(5-fluoro-1H-indol-3-yl)ethyl]urea hydrochloride In order to produce the hydrochloride (compound 19), the more nonpolar diastereoisomer of 1-(4-dimethylamino-4-phenylcyclohexyl)-3-[2-(5-fluoro-1H-indol-3-yl)ethyl]urea (140 mg, 0.33 mmole) was dissolved in ethyl methyl ketone (3 ml) and combined with trimethylchlorosilane (60 µl, 0.45 mmole). The resulting solid was filtered out and dried. The hydrochloride of the more nonpolar diastereoisomer of 1-(4-dimethylamino-4-phenylcyclohexyl)-3-[2-(5-fluoro-1H-indol-3-yl)ethyl]urea was obtained in this manner as a colorless solid with a melting point of 197-199° C. in a yield of 152 mg (100%).

In order to produce the hydrochloride (compound 20), the more polar diastereoisomer of 1-(4-dimethylamino-4-phenylcyclohexyl)-3-[2-(5-fluoro-1H-indol-3-yl)ethyl]urea (267 mg, 0.63 mmole) was dissolved in ethyl methyl ketone (5 ml) and combined with trimethylchlorosilane (120 µl, 0.95 mmole). The resulting solid was filtered out and dried. The hydrochloride of the more polar diastereoisomer of 1-(4-dimethylamino-4-phenylcyclohexyl)-3-[2-(5-fluoro-1H-indol-3-yl)ethyl]urea was obtained in this manner as a colorless solid with a melting point of 219-221° C. in a yield of 290 mg (100%).

1-(4-Dimethylamino-4-phenylcyclohexylmethyl)-3-[2-1H-indol-3-yl)ethyl]-urea

The mixture of (4-aminomethyl-1-phenyl-cyclohexyl)-dimethylamine (464.8 mg, 2.0 mmole) was added to a solution of [2-(1H-indol-3-yl)-ethyl]-carbamic acid phenyl ester (560.6 mg, 2.0 mmole) in dioxane (15 ml). The batch was then refluxed for 12 h. Working up was performed by removing the dioxane by distillation and combining the residue with water (10 ml). The batch was adjusted to pH 11 with 5M NaOH and extracted with EE (3×20 ml). A small quantity of solid was obtained. The solid, which corresponded analytically to the more polar diastereoisomer of 1-(4-dimethylamino-4-phenylcyclohexylmethyl)-3[2-(1H-indol-3-yl)ethyl]urea (100 mg, m.p. 204-208° C., 12%), was filtered out, washed with diethyl ether (2×2 ml) and dried. The combined EE extracts were washed with 1M NaOH (5 ml) and dried with $Na_2SO_4$. The solvent was removed by distillation under a vacuum. The residue was the diastereoisomeric mixture of 1-(4-dimethylamino-4-phenylcyclohexylmethyl)-3-[2-(1H-indol-3-yl)ethyl]urea, which was separated and purified by flash chromatography on silica gel (50 g). Ethanol/EE (1:1, 1100 ml) was used as eluent. The more nonpolar diastereoisomer of 1-(4-dimethylamino-4-phenylcyclohexylmethyl)-3-[2-(1H-indol-3-yl)ethyl]urea (264 mg, m.p. 159-163° C., 32%) and a further fraction of the more polar diastereoisomer of 1-(4-dimethylamino-4-phenylcyclohexylmethyl)-3-[2-(1H-indol-3-yl)ethyl]urea (55 mg, m.p. 202-207° C., 7%) were isolated in this manner.

Examples 21 and 22

1-(4-Dimethylamino-4-phenylcyclohexylmethyl)-3-[2-(1H-indol-3-yl)ethyl]urea hydrochloride The more nonpolar diastereoisomer of 1-(4-dimethylamino-4-phenylcyclohexylmethyl)-3-[2-(1H-indol-3-yl)ethyl]urea (256 mg, 0.6 mmole) was dissolved in ethyl methyl ketone (15 ml). 5M isopropanolic hydrochloric acid (184 µl, 0.92 mmole) was added dropwise at RT with stirring. After one hour's stirring at RT, a precipitate had formed. The solid was filtered out, washed with diethyl ether (3×1.5 ml) and dried under a vacuum. The hydrochloride (Example 21) of the more nonpolar urea was obtained in this manner as a colorless solid in a yield of 272 mg (99%).

The more polar diastereoisomer of 1-(4-dimethylamino-4-phenyl-cyclohexylmethyl)-3-[2-(1H-indol-3-yl)ethyl]urea (128 mg, 0.3 mmole) was dissolved in abs. ethanol (15 ml) and ethyl methyl ketone (5 ml). 5M isopropanolic hydrochloric acid (92 µl, 0.46 mmole) was added dropwise at RT with stirring. After one hour's stirring at RT, no precipitate had formed. The reaction solution was reduced to approx. 2 ml under a vacuum and combined with diethyl ether (10 ml). The tacky precipitate was mechanically detached from the flask wall. The suspension was vigorously stirred at RT for 1 h. A fine, light-colored precipitate formed. The solid was filtered out, washed with diethyl ether (3×1.5 ml) and dried under a vacuum. The hydrochloride (Example 22) of the more polar urea was obtained in this manner as a cream-colored solid in a yield of 137.2 mg (99%).

1-(4-Dimethylamino-4-phenylcyclohexylmethyl)-3-(3-phenylpropyl)urea

The diastereoisomer mixture of (4-aminomethyl-1-phenyl-cyclohexyl)-dimethylamine (465.8 mg, 2.0 mmole) was added to a solution of (3-phenylpropyl)carbamic acid phenyl ester (510.6 mg, 2.0 mmole) in dioxane (15 ml). The batch was then refluxed for 12 h. Working up was performed by removing dioxane by distillation in a rotary evaporator and combining the residue with water (10 ml). The batch was adjusted to pH 11 with 5M NaOH and extracted with EE (3×20 ml). The combined EE extracts were washed with 1M NaOH (1×5 ml) and dried with Na₂SO₄. The solvent was removed by distillation under a vacuum. The residue was the diastereoisomer mixture of 1-(4-dimethylamino-4-phenyl-cyclohexylmethyl)-3-(3-phenyl-propyl)-urea, which was separated and purified by flash chromatography on silica gel (60 g). Ethanol/EE (1:1, 1100 ml) was used as eluent. The more nonpolar diastereoisomer of 1-(4-dimethylamino-4-phenyl-cyclohexylmethyl)-3-(3-phenyl-propyl)-urea (310 mg, yellow oil, 39%) and the more polar diastereoisomer of 1-(4-dimethylamino-4-phenyl-cyclohexylmethyl)-3-(3-phenyl-propyl)-urea (55 mg, m.p. 159-165° C., 32%) were isolated in this manner.

Examples 23 and 24

1-(4-Dimethylamino-4-phenylcyclohexylmethyl)-3-(3-phenylpropyl)urea hydrochloride The more nonpolar diastereoisomer of 1-(4-dimethylamino-4-phenyl-cyclohexyl-methyl)-3-(3-phenyl-propyl)-urea (310 mg, 0.79 mmole) was dissolved in acetone (5 ml) and ethyl methyl ketone (15 ml). Chlorotrimethylsilane (150 ml, 1.2 mmole) was added dropwise with stirring at RT. After one hour's stirring, no precipitate had formed. The reaction solution was reduced to approx. 1 ml under a vacuum and combined with diethyl ether (10 ml). The mixture was then vigorously stirred at RT for 1 h. A colorless precipitate was formed. The solid was filtered out, washed with diethyl ether (3×3 ml) and dried under a vacuum. The hydrochloride of the more nonpolar diastereoisomer of 1-(4-dimethylamino-4-phenyl-cyclohexylmethyl)-3-(3-phenyl-propyl)-urea (339 mg, m.p. 85-95° C., 100%; Example 23) was obtained as a colorless solid.

The more polar diastereoisomer of 1-(4-dimethylamino-4-phenyl-cyclohexylmethyl)-3-(3-phenyl-propyl)-urea (249 mg, 0.63 mmole) was dissolved in acetone (7 ml) and ethyl methyl ketone (15 ml). Chlorotrimethylsilane (121 µl, 0.95 mmole) was added dropwise with stirring at RT. After one hour's stirring, no precipitate had formed. The reaction solution was reduced to approx. 0.5 ml under a vacuum and combined with diethyl ether (10 ml). The mixture was then vigorously stirred at RT for 1 h. An almost colorless precipitate was formed. The solid was filtered out, washed with diethyl ether (3×2.5 ml) and dried under a vacuum. The hydrochloride of the more polar diastereoisomer of 1-(4-dimethylamino-4-phenyl-cyclohexylmethyl)-3-(3-phenyl-propyl)-urea (270 mg, m.p. 100-110° C., 99%; Example 24) was obtained as a grey/colorless solid.

1-(4-Dimethylamino-4-phenylcyclohexylmethyl)-3-[2-(1H-indol-3-yl)-1-methylethyl]urea The more nonpolar diastereoisomer of (4-aminomethyl-1-phenyl-cyclohexyl)-dimethylamine (162.7 mg, 0.7 mmole) was added to a solution of [2-(1H-indol-3-yl)-1-methyl-ethyl]-carbamic acid phenyl ester (206 mg, 0.7 mmole) in dioxane (7 ml). The batch was then refluxed for 14 h. Working up was performed by pouring the reaction mixture into ice water (15 ml), adjusting the pH to 11 with 5M NaOH and extracting with ether (3×20 ml). The organic phase was dried with Na₂SO₄ and then evaporated. The residue was purified by flash chromatography on silica gel (30 g). Ethanol/EE (1:2, 400 ml) was used as eluent. The more nonpolar diastereoisomer of 1-(4-dimethylamino-4-phenyl-cyclohexylmethyl)-3-[2-(1H-indol-3-yl)-1-methyl-ethyl]-urea was obtained in this manner as a colorless solid with a melting point of 89-92° C. in a yield of 185 mg (61%).

The more polar diastereoisomer of (4-aminomethyl-1-phenyl-cyclohexyl)-dimethylamine (162.7 mg, 0.7 mmole) was added to a solution of [2-(1H-indol-3-yl)-1-methyl-ethyl]-carbamic acid phenyl ester (206 mg, 0.7 mmole) in dioxane (7 ml). The batch was then refluxed for 14 h. A precipitate formed at RT. The precipitate was filtered out, and washed once with cold dioxane (2 ml) and with diethyl ether (3×3 ml). The more polar diastereoisomer of 1-(4-dimethylamino-4-phenyl-cyclohexylmethyl)-3-[2-(1H-indol-3-yl)-1-methyl-ethyl]-urea was obtained in this manner as a colorless solid with a melting point of 140-146° C. in a yield of 231 mg (76%).

Examples 25 and 26

1-(4-Dimethylamino-4-phenylcyclohexylmethyl)-3-[2-(1H-indol-3-yl)-1-methylethyl]urea hydrochloride The more nonpolar diastereoisomer of 1-(4-dimethylamino-4-phenyl-cyclohexyl-methyl)-3-[2-(1H-indol-3-yl)-1-methyl-ethyl]-urea (157 mg, 0.36 mmole) was dissolved in ethyl methyl ketone (6 ml). Chlorotrimethylsilane (69 µl, 0.6 mmole) was added dropwise with stirring at RT. On stirring for one hour at RT, only a little precipitate formed.

The reaction solution was combined with diethyl ether (25 ml). The mixture was then vigorously stirred at RT for 1 h. A colorless precipitate was formed. The solid was filtered out, washed with diethyl ether (3×2 ml) and dried under a vacuum. The hydrochloride of the more nonpolar diastereoisomer of 1-(4-dimethylamino-4-phenyl-cyclohexylmethyl)-3-[2-(1H-indol-3-yl)-1-methyl-ethyl]-urea (163 mg, m.p. 150-155° C., 97%; Example 25) was obtained in this manner as a colorless solid.

The more polar diastereoisomer of 1-(4-dimethylamino-4-phenyl-cyclohexylmethyl)-3-[2-(1H-indol-3-yl)-1-methyl-ethyl]-urea (219 mg, 0.5 mmole) was dissolved in ethyl methyl ketone (40 ml). Chlorotrimethylsilane (95 µl, 0.75 mmole) was added dropwise with stirring at RT. After one hour's stirring at RT, no precipitate had formed. The reaction solution was reduced to 5 ml under a vacuum and combined with diethyl ether (15 ml). The mixture was then vigorously stirred at RT for 1 h. An almost colorless precipitate was formed. The solid was filtered out, washed with diethyl ether (3×3 ml) and dried under a vacuum. The hydrochloride of the more polar diastereoisomer of 1-(4-dimethylamino-4-phenyl-cyclohexylmethyl)-3-[2-(1H-indol-3-yl)-1-methyl-ethyl]-urea (219 mg, m.p. 170-174° C., 93%; Example 26) was obtained in this manner as a colorless solid.

1-(4-Dimethylamino-4-phenylcyclohexylmethyl)-3-[2-(5-fluoro-1H-indol-3-yl)ethyl]urea The diastereoisomer mixture of (4-dimethylamino-4-phenyl-cyclohexylmethyl)-carbamic acid phenyl ester (588.6 mg, 1.67 mmole) was added to a solution of 2-(5-fluoro-1H-indol-3-yl)-ethylamine (297.5 mg, 1.67 mmole) in dioxane (14 ml). The reaction mixture was refluxed for 24 h. A colorless precipitate was formed at RT. The precipitate was filtered out, washed with dioxane (1×1 ml) and with diethyl ether (4×2 ml) and then dried. The colorless solid obtained was the more polar diastereoisomer of 1-(4-dimethylamino-4-phenyl-cyclohexylmethyl)-3-[2-(5-fluoro-1H-indol-3-yl)-ethyl]-urea (220 mg, m.p. 97-101° C., 30%). The filtrate was evaporated. Apart from phenol, the residue predominantly contained the more nonpolar diastereoisomer of 1-(4-dimethylamino-4-phenyl-cyclohexylmethyl)-3-[2-(5-fluoro-1H-indol-3-yl)-ethyl]-urea. This diastereoisomer was purified by flash chromatography on silica gel (60 g). Methanol/ EE (1:1, 800 ml) was used as eluent. The more nonpolar diastereoisomer of 1-(4-dimethylamino-4-phenyl-cyclohexylmethyl)-3-[2-(5-fluoro-1H-indol-3-yl)-ethyl]-urea (187 mg, m.p. 70-73° C.) was isolated in this manner in a yield of 26%.

Examples 27 and 28

1-(4-Dimethylamino-4-phenylcyclohexylmethyl)-3-[2-(5-fluoro-1H-indol-3-yl)ethyl]urea citrate The more nonpolar diastereoisomer of 1-(4-dimethylamino-4-phenyl-cyclohexyl-methyl)-3-[2-(5-fluoro-1H-indol-3-yl)-ethyl]-urea (187 mg, 0.428 mmole) was dissolved in abs. ethanol (3.5 ml). The citric acid (83 mg, 0.43 mmole) was added in a single portion with stirring at approx. 40° C. After two hours' stirring at RT, no precipitate had formed. The reaction mixture was combined with diethyl ether (20 ml) and stirred for a further 1 h at RT. After brief cooling, the colorless precipitate was filtered out, washed with cold diethyl ether (3×3 ml) and dried under a vacuum. The more nonpolar diastereoisomer of 1-(4-dimethylamino-4-phenyl-cyclohexylmethyl)-3-[2-(5-fluoro-1H-indol-3-yl)-ethyl]-urea citrate (214 mg, 80%, Example 27) was a colorless solid.

The more polar diastereoisomer of 1-(4-dimethylamino-4-phenyl-cyclohexylmethyl)-3-[2-(5-fluoro-1H-indol-3-yl)-ethyl]-urea (208 mg, 0.476 mmole) was dissolved in abs. ethanol (3.5 ml). The citric acid (92.5 mg, 0.481 mmole) was added in a single portion with stirring at approx. 40° C. After two hours' stirring at RT, no precipitate had formed. The reaction mixture was reduced to approx. 1 ml of solution and combined in portions with diethyl ether (20 ml). The resultant precipitate was filtered out after 1 h, washed with ether (3×3 ml) and dried under a vacuum. The more polar diastereoisomer of 1-(4-dimethylamino-4-phenyl-cyclohexylmethyl)-3-[2-(5-fluoro-1H-indol-3-yl)-ethyl]-urea citrate (230 mg, 77%, Example 28) was a colorless solid.

Examples 29 and 30

1-(4-Dimethylamino-4-phenylcyclohexyl)-3-[2-(1H-indol-3-yl)-ethyl]thiourea citrate In order to produce the citrate, the more nonpolar diastereoisomer of 1-(4-dimethylamino-4-phenyl-cyclohexyl)-3-[2-(1H-indol-3-yl)-ethyl]-thiourea (433 mg, 1.03 mmole) was dissolved in hot ethanol (15 ml) and combined with a likewise hot solution of citric acid (435 mg, 2.27 mmole) in ethanol (2 ml). After cooling to approx. 5° C., the batch was left to stand for 4 h. The resultant solid was filtered out. The more nonpolar diastereoisomer of 1-(4-dimethylamino-4-phenyl-cyclohexyl)-3-[2-(1H-indol-3-yl)-ethyl]-thiourea could be obtained in this manner as a colorless solid (Example 29, m.p. 165-170° C.) in a yield of 630 mg (100%).

In order to produce the citrate, the more polar diastereoisomer of 1-(4-dimethylamino-4-phenyl-cyclohexyl)-3-[2-(1H-indol-3-yl)-ethyl]-thiourea (185 mg, 0.44 mmole) was dissolved in hot ethanol (7 ml) and combined with a likewise hot solution of citric acid (186 mg, 0.97 mmole) in ethanol (1 ml). After cooling to approx. 5° C., the batch was left to stand for 4 h. The resultant solid was filtered out. The more polar diastereoisomer of 1-(4-dimethylamino-4-phenyl-cyclohexyl)-3-[2-(1H-indol-3-yl)-ethyl]-thiourea could be obtained in this manner as a colorless solid (Example 30, m.p. 98-103° C.) in a yield of 269 mg (100%).

1-(4-Dimethylamino-4-phenylcyclohexyl)-3-(4-phenylpropyl)thiourea

Phenylpropylamine (285 µl, 2 mmole) was dissolved in dry chloroform (15 ml) and combined with triethylamine (555 µl, 4 mmole). Thiophosgene (153 µl, 2 mmole) was added to this mixture. After a reaction time of 16 h, the diastereoisomer mixture of N,N-dimethyl-1-phenyl-cyclohexane-1,4-diamine was added and stirring was continued for a further 16 h at RT. Working up was performed by extracting the batch with saturated $NaHCO_3$ solution (3×20 ml). The organic phase was dried with $Na_2SO_4$ and evaporated. The product was a mixture of two diastereoisomers and could be purified by column chromatography [silica gel 60 (50 g); methanol (500 ml)]. The more polar diastereoisomer of 1-(4-dimethylamino-4-phenyl-cyclohexyl)-3-(3-phenyl-propyl)-thiourea was obtained as a colorless foam in a yield of 205 mg (25%). The more nonpolar diastereoisomer of 1-(4-dimethylamino-4-phenyl-cyclohexyl)-3-(3-phenyl-propyl)-thiourea was obtained as a colorless foam in a yield of 410 mg (50%).

Examples 31 and 32

1-(4-Dimethylamino-4-phenylcyclohexyl)-3-(4-phenyl-propyl)thiourea citrate

In order to produce the citrate, the more nonpolar diastereoisomer of 1-(4-dimethylamino-4-phenyl-cyclohexyl)-3-(3-phenyl-propyl)-thiourea (410 mg, 1 mmole) was dissolved in hot ethanol (15 ml) and combined with a likewise hot solution of citric acid (422 mg, 2.2 mmole) in ethanol (2 ml). After cooling to approx. 5° C., the batch was left to stand for 4 h. The resultant solid was filtered out. The more nonpolar diastereoisomer of 1-(4-dimethylamino-4-phenyl-cyclohexyl)-3-(3-phenyl-propyl)-thiourea citrate was obtained in this manner as a colorless solid (Example 31, melting point: 63-67° C.) in a yield of 588 mg (100%).

In order to produce the citrate, the more polar diastereoisomer of 1-(4-dimethylamino-4-phenyl-cyclohexyl)-3-(3-phenyl-propyl)-thiourea (205 mg, 0.5 mmole) was dissolved in hot ethanol (7 ml) and combined with a likewise hot solution of citric acid (211 mg, 1.1 mmole) in ethanol (1 ml). After cooling to approx. 5° C., the batch was left to stand for 4 h. The resultant solid was filtered out. The more polar diastereoisomer of 1-(4-dimethylamino-4-phenyl-cyclohexyl)-3-(3-phenyl-propyl)-thiourea was obtained in this manner as a colorless solid (Example 32, melting point: 75-80° C.) in a yield of 294 mg (100%).

1-(4-Dimethylamino-4-phenylcyclohexyl)-3-[2-(1H-indol-3-yl)methyl-ethyl]thiourea 2-(1H-indol-3-yl)-1-methyl-ethylamine (349 mg, 2 mmole) was dissolved in dry chloroform (10 ml) and combined with triethylamine (555 μl, 4 mmole). Thiophosgene (153 μl, 2 mmole) was added to this mixture. After a reaction time of 16 h, the diastereoisomer mixture of N,N-dimethyl-1-phenyl-cyclohexane-1,4-diamine was added and stirring was continued for a further 16 h at RT. Working up was performed by extracting the batch with saturated NaHCO$_3$ solution (3×20 ml). The organic phase was dried with Na$_2$SO$_4$ and evaporated. The product was a mixture of two diastereoisomers and could be purified by column chromatography [silica gel 60 (50 g); methanol (500 ml)]. The more polar diastereoisomer of 1-(4-dimethylamino-4-phenyl-cyclohexyl)-3-[2-(1H-indol-3-yl)-1-methyl-ethyl]-thiourea was obtained as a colorless solid in a yield of 256 mg (29%). The more nonpolar diastereoisomer of 1-(4-dimethylamino-4-phenyl-cyclohexyl)-3-[2-(1H-indol-3-yl)-1-methyl-ethyl]-thiourea was obtained as a colorless solid in a yield of 324 mg (37%).

Examples 33 and 34

1-(4-Dimethylamino-4-phenylcyclohexyl)-3-[2-(1H-indol-3-yl)methyl-ethyl]thiourea citrate In order to produce the citrate, the more nonpolar diastereoisomer of 1-(4-dimethylamino-4-phenyl-cyclohexyl)-3-[2-(1H-indol-3-yl)-1-methyl-ethyl]-thiourea (324 mg, 0.75 mmole) was dissolved in hot ethanol (10 ml) and combined with a likewise hot solution of citric acid (316 mg, 1.65 mmole) in ethanol (1.5 ml). After cooling to approx. 5° C., the batch was left to stand for 4 h. The resultant solid was filtered out. The more nonpolar diastereoisomer of 1-(4-dimethylamino-4-phenyl-cyclohexyl)-3-[2-(1H-indol-3-yl)-1-methyl-ethyl]-thiourea citrate could be obtained in this manner as a colorless solid (Example 33, melting point: 145-148° C.) in a yield of 467 mg (100%).

In order to produce the citrate, the more polar diastereoisomer of 1-(4-dimethylamino-4-phenyl-cyclohexyl)-3-[2-(1H-indol-3-yl)-1-methyl-ethyl]-thiourea (256 mg, 0.59 mmole) was dissolved in hot ethanol (8 ml) and combined with a likewise hot solution of citric acid (249 mg, 1.3 mmole) in ethanol (1 ml). After cooling to approx. 5° C., the batch was left to stand for 4 h. The resulting solid was filtered out. The more polar diastereoisomer of 1-(4-dimethylamino-4-phenyl-cyclohexyl)-3-[2-(1H-indol-3-yl)-1-methyl-ethyl]-thiourea citrate could be obtained in this manner as a colorless solid (Example 34, melting point: 108-113° C.) in a yield of 369 mg (100%).

3-(4-Dimethylamino-4-phenyl-cyclohexyl)-acrylonitrile

The diastereoisomeric mixture of 4-dimethylamino-4-phenyl-cyclohexyl-carbaldehyde (518 mg, 2.24 mmole) and cyanomethanephosphonic acid diethyl ester (476.7 g, 2.69 mmole) were dissolved in DCM (10 ml). This solution was added dropwise with ice water cooling at a temperature of 5 to 10° C. to a solution of 40% aqueous NaOH (5 ml). Working up was performed by combining the batch after 2 h with ice (20 g) and DCM (10 ml). The phases were separated. The aqueous phase was extracted with DCM (2×5 ml). The combined extracts were washed with saturated NaCl-solution (4×5 ml), dried and evaporated. The residue was purified by chromatography [silica gel (70 g) eluent: EE/MeOH 500 ml (10:1) and 700 ml (4:1)]. The four diastereoisomers of 3-(4-dimethylamino-4-phenyl-cyclohexyl)-acrylonitrile were obtained in this manner in an overall yield of 71% (406 mg).

[4-(3-Aminopropyl)-1-phenylcyclohexyl]dimethylamine 3-(4-Dimethylamino-4-phenyl-cyclohexyl)-acrylonitrile (400 mg, 1.57 mmole) was dissolved in methanol (25 ml). Nickel(II) chloride hexahydrate (747.6 mg, 3.14 mmole) was added to the solution. NaBH$_4$ (594 mg, 15.7 mmole) was then added in portions with ice water cooling. A black precipitate was formed accompanied by evolution of hydrogen. Once addition was complete, stirring was continued at 20° C. for 1 h. Working up was performed by combining the reaction mixture with 1M hydrochloric acid (15 ml). The black precipitate was filtered out on Celite and thoroughly washed with 1M hydrochloric acid (3×7 ml). The hydrochloric, aqueous-methanolic solution was reduced to half its volume in order to remove the methanol. The remaining aqueous phase was extracted with ether (3×15 ml) to remove neutral substances. The batch was then alkalised (pH 11) by addition of 2M NaOH, resulting in the formation of a bulky precipitate which did not dissolve even on addition of EE. The precipitate was filtered out and washed with water (1×3 ml) and EE (3×5 ml). The two phases of the clear mother liquor were separated. The aqueous phase was extracted with EE (3×15 ml). The combined extracts were washed with NaCl-solution (2×10 ml), dried over sodium sulfate and the solvent removed by distillation. The resultant residue was the mixture of the diastereoisomers of [4-(3-aminopropyl)-1-phenylcyclohexyl]dimethylamine (203 mg, light yellow oil, 50%).

[2-(1H-Indol-3-yl)ethyl]carbamic acid phenyl ester

Chloroformic acid phenyl ester (3.29 g, 21.0 mmole) and pyridine (1.74 g, 22.0 mmole) were added to a solution of tryptamine (3.2 g, 20.0 mmole) in abs. DCM (50 ml). Stirring was then performed for 24 h at RT. Working up was performed by extracting the batch with water (2×20 ml), with 1M HCl (2×20 ml) and 1M NaOH (2×20 ml). The organic phase was dried with Na$_2$SO$_4$ and then evaporated. [2-(1H-Indol-3-yl)ethyl]carbamic acid phenyl ester was obtained as a colorless solid with an m.p. of 44-46° C. in a yield of 5.58 g (100%).

Examples 35 and 36

1-[3-(4-Dimethylamino-4-phenyl-cyclohexyl)-propyl]-3-[2-(1H-indol-3-yl)-ethyl]-urea The mixture of [4-(3-aminopropyl)-1-phenyl-cyclohexyl]-dimethylamine (380 mg, 1.46 mmole) was added to a solution of [2-(1H-indol-3-yl)ethyl]carbamic acid phenyl ester (409 mg, 1.46 mmole) in dioxane (10 ml). The batch was then refluxed for 12 h. Working up was performed by removing the dioxane by distillation and combining the residue with water (10 ml). The batch was adjusted to pH 11 with 5M NaOH and extracted with EE (3×20 ml). The combined EE extracts were washed with 1M NaOH (5 ml) and dried with Na$_2$SO$_4$. The solvent was removed by distillation under a vacuum. The residue was the diastereoisomeric mixture of 1-[3-(4-dimethylamino-4-phenyl-cyclohexyl)-propyl]-3-[2-(1H-indol-3-yl)-ethyl]-urea, which was separated and purified by flash chromatography on silica gel (70 g). Methanol/EE (3:1, 1500 ml; 1:1, 500 ml; and 1:2, 1000 ml) was used as eluent. The more nonpolar diastereoisomer of 1-[3-(4-dimethylamino-4-phenyl-cyclohexyl)-propyl]-3-[2-(1H-indol-3-yl)-ethyl]-urea (Example 35, 95 mg, m.p. 126° C., 15%) and the more polar diastereoisomer of 1-[3-(4-dimethylamino-4-phenyl-cyclohexyl)-propyl]-3-[2-(1H-indol-3-yl)-ethyl]-urea (Example 36, 116 mg, m.p. 57° C., 18%) were isolated in this manner.

1-(4-Dimethylamino-4-phenylcyclohexylmethyl)-3-[2-(1H-indol-3-yl)ethyl]-thiourea Tryptamine (320.4 mg, 2 mmole) was dissolved in dry chloroform (10 ml) and combined with triethylamine (533 μl, 4 mmole). The mixture was cooled to −5° C. Thiophosgene (153.3 μl, 2 mmole) was then added dropwise, resulting in the formation of a precipitate. After a reaction time of 18 h at RT, (4-aminomethyl-1-phenyl-cyclohexyl)-dimethylamine (464.74 mg, 2 mmole) dissolved in chloroform (5 ml) was added. After 20 h stirring at RT, the reaction mixture was clear. Working up was performed by washing the batch with saturated NaHCO$_3$ solution (3×5 ml) and water (5 ml). The organic phase was dried with Na$_2$SO$_4$ and evaporated. The product was a mixture of two diastereoisomers. These were purified and separated by column chromatography [silica gel 60 (70 g); eluent: MeOH/EE 1:1 (1500 ml)]. The more nonpolar diastereoisomer of 1-(4-dimethylamino-4-phenylcyclohexylmethyl)-3-[2-(1H-indol-3-yl)ethyl]thiourea (266 mg, m.p. 84-87° C., 31%) and also the more polar diastereoisomer of 1-(4-dimethylamino-4-phenylcyclohexylmethyl)-3-[2-(1H-indol-3-yl)ethyl]thiourea (274 mg, m.p. 92-95° C., 32%) were light beige solids.

Examples 37 and 38

1-(4-Dimethylamino-4-phenylcyclohexylmethyl)-3-[2-(1H-indol-3-yl)-ethyl]thiourea citrate In order to produce the citrate, the more nonpolar diastereoisomer of 1-(4-dimethylamino-4-phenylcyclohexylmethyl)-3-[2-(1H-indol-3-yl)ethyl]thiourea (253 mg, 0.582 mmole) was dissolved in ethanol (4 ml) at RT and combined with a solution of citric acid (123 mg, 0.588 mmole) in ethanol (1 ml). After 2 h, the batch was combined with 20 ml ether and stirred for 18 h. The resultant solid was filtered out, washed with ether (3×2 ml) and dried. The nonpolar diastereoisomer of 1-(4-dimethylamino-4-phenylcyclohexylmethyl)-3-[2-(1H-indol-3-yl)ethyl]-thiourea citrate could be obtained in this manner as a light yellow solid in a yield of 297 mg (Example 37, 81%).

In order to produce the citrate, the more polar diastereoisomer of 1-(4-dimethylamino-4-phenylcyclohexylmethyl)-3-[2-(1H-indol-3-yl)ethyl]thiourea (262 mg, 0.603 mmole) was dissolved in ethanol (5 ml) and combined with a solution of citric acid (117 mg, 0.608 mmole) in ethanol (1 ml). A bulky precipitate immediately formed, the structure of which improved on addition of ether (20 ml). After 20 h stirring at RT, the resultant solid was filtered out. The more polar diastereoisomer of 1-(4-dimethylamino-4-phenylcyclohexylmethyl)-3-[2-(1H-indol-3-yl)ethyl]thiourea citrate (Example 38, 317 mg, 84%) was a beige, hygroscopic solid.

1-(4-Dimethylamino-4-phenylcyclohexylmethyl)-3-[2-(1H-indol-3-yl)-1-methylethyl]thiourea

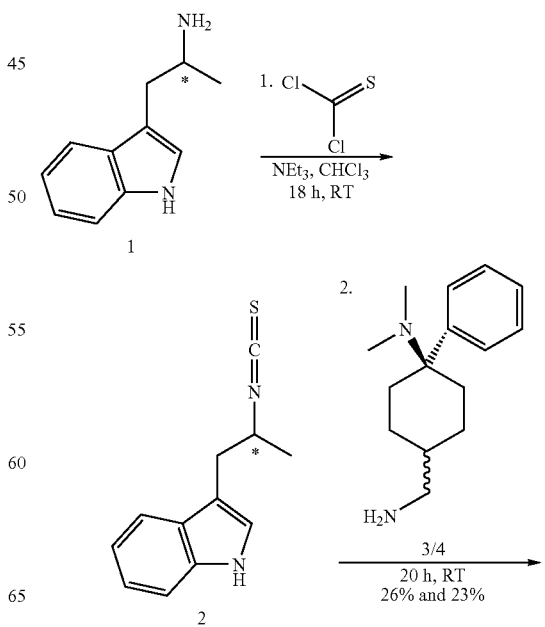

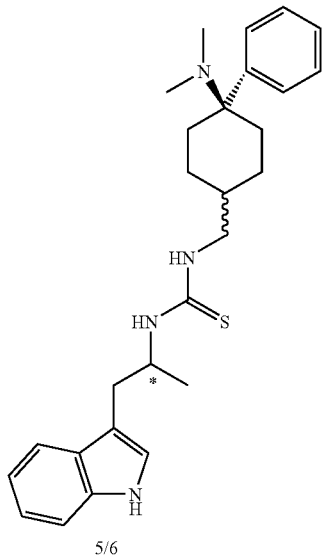

5/6

α-methyltryptamine (261.4 mg, 1.5 mmole) was dissolved in dry chloroform (15 ml) and combined with triethylamine (422 μl, 3 mmole). The mixture was cooled to −5° C. Thiophosgene (115 μl, 1.5 mmole) dissolved in chloroform (10 ml) was then added dropwise, resulting in the formation of a precipitate. After a reaction time of 18 h at RT, (4-aminomethyl-1-phenyl-cyclohexyl)-dimethylamine (348.55 mg, 1.5 mmole) dissolved in chloroform (10 ml) was added. After 20 h stirring at RT, the reaction mixture was clear. Working up was performed by washing the batch with saturated NaHCO$_3$ solution (3×5 ml) and water (5 ml). The organic phase was dried with Na$_2$SO$_4$ and evaporated. The product was a mixture of two diastereoisomers. These were purified and separated by column chromatography [silica gel 60 (70 g); eluent: MeOH/EE 1:5 (1500 ml)]. The more nonpolar diastereoisomer of 1-(4-dimethylamino-4-phenylcyclohexylmethyl)-3-[2-(1H-indol-3-yl)-1-methylethyl]thiourea (177 mg, m.p. 99-104° C., 26%) and also the more polar diastereoisomer of 1-(4-dimethylamino-4-phenylcyclohexylmethyl)-3-[2-(1H-indol-3-yl)-1-methylethyl]thiourea (152 mg, m.p. 93-95° C., 23%) were colorless solids.

Examples 39 and 40

1-(4-Dimethylamino-4-phenylcyclohexylmethyl)-3-[2-(1 H-indol-3-yl)-1-methylethyl]thiourea citrate In order to produce the citrate, the more nonpolar diastereoisomer of 1-(4-dimethylamino-4-phenylcyclohexylmethyl)-3-[2-(1H-indol-3-yl)-1-methylethyl]-thiourea (167 mg, 0.37 mmole) was dissolved in ethanol (4 ml) at RT and combined with a solution of citric acid (78.7 mg, 0.41 mmole) in ethanol (1 ml). After 1 h, a tacky precipitate could be seen on the flask wall and was detached mechanically. The batch was then combined with ether (35 ml) and stirred for 20 h. The resultant solid was filtered out, washed with ether (3×3 ml) and dried. The nonpolar diastereoisomer of 1-(4-dimethylamino-4-phenyl-cyclohexylmethyl)-3-[2-(1H-indol-3-yl)-1-methylethyl]thiourea citrate was obtained in this way as a colorless solid (Example 39) in a yield of 206 mg (87%).

In order to produce the citrate, the more polar diastereoisomer of 1-(4-dimethylamino-4-phenylcyclohexylmethyl)-3-[2-(1H-indol-3-yl)-1-methylethyl]-thiourea (140 mg, 0.31 mmole) was dissolved in ethanol (4 ml) and combined with a solution of citric acid (65.9 mg, 0.34 mmole) in ethanol (1 ml). Only a little precipitate formed. The mixture was thus combined with ether (50 ml). After 20 h stirring at RT, the resultant solid was filtered out. The more polar diastereoisomer of 1-(4-dimethylamino-4-phenylcyclohexylmethyl)-3-[2-(1H-indol-3-yl)-1-methylethyl]thiourea citrate was obtained in this manner as a colorless solid (Example 40) in a yield of 185.5 mg (93%).

2-[3-(4-Dimethylamino-4-phenylcyclohexylmethyl) thioureido]-3-(1H-indol-3-yl)propionic acid methyl ester Tryptophan methyl ester hydrochloride (382 mg, 1.5 mmole) was dissolved in dry chloroform (15 ml) and combined with triethylamine (633 μl, 4.5 mmole). The mixture was cooled to −5° C. Thiophosgene (115 μl, 1.5 mmole) dissolved in chloroform (10 ml) was then added dropwise, resulting in the formation of a precipitate. After 18 h stirring at RT, the reaction mixture was clear. (4-Aminomethyl-1-phenyl-cyclohexyl)-dimethylamine (348.55 mg, 1.5 mmole), dissolved in chloroform (10 ml), was added at RT. After a reaction time of 48 h, the batch was washed with saturated NaHCO$_3$ solution (3×5 ml) and water (5 ml). The organic phase was dried with Na$_2$SO$_4$ and evaporated. The product was a mixture of two diastereoisomers. These were purified and separated by column chromatography [silica gel 60 (100 g); eluent: MeOH/EE 1:4 (1500 ml) and MeOH/EE 1:1 (500 ml)]. The more nonpolar diastereoisomer of 2-[3-(4-dimethylamino-4-phenylcyclohexylmethyl)thioureido]-3-(1H-indol-3-yl)propionic acid methyl ester (193 mg, m.p. 178-183° C., 26%) and also the more polar diastereoisomer of 2-[3-(4-dimethylamino-4-phenylcyclohexyl-methyl)thioureido]-3-(1H-indol-3-yl)propionic acid methyl ester (157 mg, m.p. 228-234° C., 21%) were light yellow solids.

Examples 41 and 42

2-[3-(4-Dimethylamino-4-phenylcyclohexylmethyl) thioureido]-3-(1H-indol-3-yl)propionic acid methyl ester citrate In order to produce the citrate, the more nonpolar diastereoisomer of 2-[3-(4-dimethylamino-4-phenylcyclohexylmethyl)thioureido]-3-(1H-indol-3-yl)propionic acid methyl ester (135 mg, 0.274 mmole) was dissolved in hot ethanol (11 ml) and combined with a solution of citric acid (57.9 mg, 0.3 mmole) in ethanol (1 ml). After 4 h, no precipitate was visible. Ethanol was removed by distillation down to a volume of 2 ml and the mixture was slowly combined with ether (30 ml). The suspension was stirred for 20 h at RT and cooled for 2 h in the refrigerator. The resultant solid was filtered out, washed with cold ether (2×1 ml) and dried. The nonpolar diastereoisomer of 2-[3-(4-dimethylamino-4-phenylcyclohexylmethyl)thioureido]-3-(1H-indol-3-yl)propionic acid methyl ester citrate could be obtained in this manner as a yellow solid (Example 41, m.p. 158-163° C.) in a yield of 165 mg (88%).

In order to produce the citrate, the more polar diastereoisomer of 2-[3-(4-dimethylamino-4-phenylcyclohexylmethyl)thioureido]-3-(1H-indol-3-yl)propionic acid methyl ester (156 mg, 0.317 mmole) was suspended in hot ethanol (50 ml) and combined with a solution of citric acid (66.9 mg, 0.35 mmole) in ethanol (1 ml). The more polar urea dissolved immediately on addition of the citric acid. No precipitate formed at RT. Ethanol was removed by distillation down to a volume of 3 ml and the mixture was slowly combined with ether (30 ml). The suspension was stirred for 20 h at RT and cooled for 2 h in the refrigerator. The resultant solid was filtered out, washed with cold ether (2×1 ml) and dried. The more polar diastereoisomer of 2-[3-(4-dimethylamino-4-phenylcyclohexyl-methyl)thioureido]-3-(1H-indol-3-yl)propionic acid methyl ester citrate was obtained in this manner as a light yellow solid (Example 42, m.p. 167-172° C.) in a yield of 207 mg (95%).

(4-Dimethylamino-4-phenylcyclohexylidene)acetonitrile

4-Dimethylamino-4-phenyl-cyclohexanone (10.85 g, 50 mmole) and cyanomethanephosphonic acid diethyl ester (10.65 g, 12 mmole) were dissolved in DCM (100 ml). This solution was added dropwise with ice water cooling at a temperature of 5 to 10° C. with vigorous stirring to a solution of 40% aqueous NaOH (50 ml) and stirred for 2 h at RT. Working up was performed by combining the batch with ice (100 g). The organic phase was separated off. The aqueous phase was extracted with DCM (3×40 ml). The combined extracts were washed with saturated NaCl-solution (50 ml), dried over $Na_2SO_4$ and then evaporated. (4-Dimethylamino-4-phenylcyclohexylidene)acetonitrile was obtained as a yellow oil in a yield of 95% (11.4 g).

[4-(2-Aminoethyl)-1-phenylcyclohexyl]dimethylamine (4-Dimethylamino-4-phenylcyclohexylidene)acetonitrile (1.16 g, 4.8 mmole) was dissolved in methanol (30 ml). Nickel(II) chloride hexahydrate (2.28 g, 9.6 mmole) was added to this solution. $NaBH_4$ (1.82 mg, 48 mmole) was then added in portions with stirring and ice water cooling. Once addition was complete, stirring was continued at RT for 1 h. The resultant black nickel boride was removed by suction filtration after addition of 2M hydrochloric acid (15 ml) and washed with 2M hydrochloric acid (3×10 ml). The hydrochloric, aqueous-methanolic solution was reduced to half its volume in order to remove the methanol. The remaining aqueous phase was extracted with ether (3×10 ml) to remove neutral substances. The aqueous phase was then alkalised by addition of conc. aqueous ammonia solution and again extracted with ether (3×20 ml). The combined extracts were washed with saturated NaCl-solution (30 ml), dried over $Na_2SO_4$ and then evaporated. The resultant crude product could be purified by column chromatography [silica gel 60 (100 g); MeOH (1000 ml)]. However, this did not result in separation of the diastereoisomers. [4-(2-Aminoethyl)-1-phenylcyclohexyl]dimethylamine was obtained as a colorless oil in a yield of 643 mg (54%).

1-[2-(4-Dimethylamino-4-phenylcyclohexyl)ethyl]-3-[2-(1H-indol-3-yl)-ethyl]thiourea Tryptamine (320 mg, 2 mmole) was dissolved in dry chloroform (10 ml) and combined with triethylamine (555 μl, 4 mmole). Thiophosgene (153 μl, 2 mmole) was added to this mixture. After a reaction time of 16 h, [4-(2-aminoethyl)-1-phenylcyclohexyl]dimethylamine (491 mg, 2 mmole) was added and stirring continued for a further 16 h at RT. Working up was performed by extracting the batch with saturated $NaHCO_3$ solution (3×20 ml). The organic phase was dried with $Na_2SO_4$ and evaporated. The product was a mixture of the expected diastereoisomers and could be purified by column chromatography [silica gel 60 (100 g); MeOH (1000 ml)]. The more polar diastereoisomer of 1-[2-(4-dimethylamino-4-phenylcyclohexyl)ethyl]-3-[2-(1H-indol-3-yl)ethyl]thiourea was obtained as a colorless oil in a yield of 330 mg (36%). The more nonpolar diastereoisomer of 1-[2-(4-dimethylamino-4-phenylcyclohexyl)ethyl]-3-[2-(1H-indol-3-yl)ethyl]thiourea was obtained as a colorless oil in a yield of 230 mg (25%).

Example 43

1-[2-(4-Dimethylamino-4-phenylcyclohexyl)ethyl]-3-[2-(1H-indol-3-yl)-ethyl]thiourea hydrochloride In order to produce the hydrochloride, the more nonpolar diastereoisomer of 1-[2-(4-dimethylamino-4-phenylcyclohexyl)ethyl]-3-[2-(1H-indol-3-yl)ethyl]thiourea (230 mg, 0.5 mmole) was dissolved in ethyl methyl ketone (5 ml) and combined with trimethylchlorosilane (2.5 ml, 26.8 mmole). The colorless solid which precipitated out was removed by suction filtration after 2 h, washed with ethyl methyl ketone (3×5 ml) and then dried. The more nonpolar diastereoisomer of 1-[2-(4-dimethylamino-4-phenylcyclohexyl)-ethyl]-3-[2-(1H-indol-3-yl)ethyl]thiourea hydrochloride was obtained in this manner as a colorless solid (Example 43, m.p. 130-138° C.) in a yield of 240 mg (99%).

Example 44

1-[2-(4-Dimethylamino-4-phenylcyclohexyl)ethyl]-3-[2-(1H-indol-3-yl)-ethyl]thiourea citrate In order to produce the citrate, the more polar diastereoisomer of 1-[2-(4-dimethylamino-4-phenylcyclohexyl)ethyl]-3-[2-(1H-indol-3-yl)ethyl]thiourea (330 mg, 0.71 mmole) was dissolved in hot ethanol (4 ml) and combined with a likewise hot solution of citric acid (137 mg, 0.71 mmole) in ethanol (1 ml). After cooling to approx. 5° C., the batch was left to stand for 4 h. Since no solid precipitated out, the ethanol was removed by distillation. The more polar diastereoisomer of 1-[2-(4-dimethylamino-4-phenylcyclohexyl)ethyl]-3-[2-(1H-indol-3-yl)-ethyl]thiourea citrate was obtained in this manner as a colorless foam (Example 44, melting point: 90-95° C.) in a yield of 467 mg (100%).

Measurement of ORL1 Binding

The cyclohexane compounds of the general formula I were investigated in a receptor binding assay with $^3H$-nociceptin/Orphanin FQ with membranes of recombinant CHO-ORL1 cells. This test system was carried out in accordance with the method proposed by Ardati et al. (Mol. Pharmacol., 51, 1997, p. 816-824). The concentration of $^3H$-nociceptin/Orphanin FQ in these tests was 0.5 nM. The binding assays were performed with 20 μg portions of membrane protein per 200 μl batch in 50 mM Hepes, pH 7.4, 10 mM $MgCl_2$ and 1 mM EDTA. Binding to the ORL1 receptor was determined using 1 mg portions of WGA-SPA Beads (Amersham-Pharmacia, Freiburg), by one hour's incubation of the batch at room temperature and subsequent measurement in a Trilux scintillation counter (Wallac, Finland). Affinity is stated in Table 1 as a $K_i$ value or % inhibition at c=1 μM.

Measurement of Binding to Opiate Receptors

In a manner similar to Example 21, binding of the cyclohexane compounds of the general formula I was investigated in a receptor binding assay using the method known to the person skilled in the art for the measurement of binding to μ-, δ- and κ-opiate receptors (μ-, δ- and κ-OR). Affinity is stated in Table 1 as a $K_i$ value or % inhibition at c=1 μM.

Analgesic Testing by Tail Flick Test in Mice

The mice were each individually put in a test cage and the base of the tail was exposed to the focused heat flux from an electric lamp (tail flick type 50/08/1.bc, Labtec, Dr. Hess). The lamp intensity was so set that the time from switching on of the lamp until sudden flicking away of the tail (pain latency) in untreated mice amounted to 3 to 5 seconds. Prior to administration of the solutions containing the compound according to the invention or the respective comparison solutions, the mice were pre-tested twice within five minutes and the average value of these measurements was calculated as a pre-test average value.

The solutions of the compound according to the invention of the general formula I and the comparison solutions were then administered intravenously. Pain was measured in each case 10, 20, 40 and 60 minutes after intravenous administration. The analgesic action was determined as an increase in pain latency (% of the maximum possible antinociceptive effect) in accordance with the following formula:

$$[(T_1-T_0)/(T_2-T_0)] \times 100$$

In this formula, the time $T_0$ is the latency time prior to administration, the time $T_1$ is the latency time after administration of the active ingredient combination and the time $T_2$ is the maximum exposure period (12 seconds).

The compounds according to the invention which were investigated exhibited an analgesic action according to Table 1.

TABLE 1

| No. | ORL1 $K_i$ [μM] or % inhibition [1 μM] | μ $K_i$ [μM] or % inhibition [1 μM] | Tail flick (mouse, i.v.) $ED_{50}$ [mg/kg] or % inhibition (dose [mg/kg]) |
|---|---|---|---|
| 1 | 0.0028 | 0.0006 | 65% (1) |
| 2 | 0.1 | 94% | |
| 3 | 0.0011 | 0.0013 | |
| 4 | 0.051 | 99% | |
| 5 | 0.0043 | 0.0018 | |
| 6 | 53% | 0.065 | |
| 7 | 0.0027 | 0.0011 | |
| 8 | 64% | 0.053 | |
| 9 | 0.0003 | 0.0009 | |
| 10 | 0.01 | 0.05 | |
| 11 | 0.0046 | 0.001 | |
| 12 | 46% | 0.18 | |
| 13 | 0.031 | 0.0124 | 60% (10) |
| 14 | 32% | 50% | |
| 15 | 0.013 | 0.0032 | 69% (10) |
| 16 | 43% | 71% | |
| 17 | 0.0015 | 0.0008 | |
| 18 | 0.036 | 0.024 | |
| 19 | 0.0013 | 0.0011 | |
| 20 | 0.034 | 0.0077 | |
| 21 | 0.037 | 0.011 | |
| 22 | 0.0079 | 0.001 | |
| 23 | 0.051 | 0.0093 | |
| 24 | 0.012 | 0.024 | |
| 25 | 0.018 | 0.0061 | |
| 26 | 0.0089 | 0.0033 | |
| 27 | 0.043 | 0.011 | |
| 28 | 0.0069 | 0.0009 | |
| 29 | 0.051 | 0.025 | |
| 30 | 0.008 | 0.0031 | |
| 31 | 0.0024 | 0.012 | |
| 32 | 0.088 | 0.159 | |

TABLE 1-continued

| No. | ORL1 $K_i$ [μM] or % inhibition [1 μM] | μ $K_i$ [μM] or % inhibition [1 μM] | Tail flick (mouse, i.v.) $ED_{50}$ [mg/kg] or % inhibition (dose [mg/kg]) |
|---|---|---|---|
| 33 | 0.0039 | 0.0053 | |
| 34 | 0.036 | 0.19 | |

Parenteral Solution of a Cyclohexylurea Compound According to the Invention 38 g of one of the cyclohexylurea compounds according to the invention, specifically Example 9, is dissolved at room temperature in 1 liter of water for injection and then adjusted to isotonic conditions by addition of anhydrous glucose for injection.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A cyclohexylurea compound corresponding to formula I:

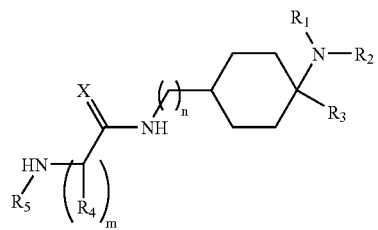

wherein
n=0-3,
m=0-2,
X=O or S (where m=0),
$R^1$ and $R^2$ are independently selected from the group consisting of H; $C_{1-8}$ alkyl and $C_{3-8}$ cycloalkyl, in each case saturated or unsaturated, branched or unbranched, mono- or polysubstituted or unsubstituted; aryl and heteroaryl, in each case mono- or polysubstituted or unsubstituted; and aryl, $C_{3-8}$ cycloalkyl or heteroaryl, in each case mono- or polysubstituted or unsubstituted, bound via $C_{1-3}$ alkylene, or
$R^1$ and $R^2$ together form a ring and denote $CH_2CH_2OCH_2CH_2$, $CH_2CH_2NR^6CH_2CH_2$ or $(CH_2)_{3-6}$, wherein
$R^6$ is selected from the group consisting of H; $C_{1-8}$ alkyl and $C_{3-8}$ cycloalkyl, in each case saturated or unsaturated, branched or unbranched, mono- or polysubstituted or unsubstituted; aryl and heteroaryl, in each case mono- or polysubstituted or unsubstituted; and aryl, $C_{3-8}$ cycloalkyl or heteroaryl bound via $C_{1-3}$ alkylene, in each case mono- or polysubstituted or unsubstituted;
$R^3$ is selected from the group consisting of $C_{1-8}$ alkyl and $C_{3-8}$ cycloalkyl, in each case saturated or unsaturated, branched or unbranched, mono- or polysubstituted or unsubstituted; aryl and heteroaryl, in each case unsubstituted or mono- or polysubstituted; and aryl, $C_{3-8}$ cycloalkyl and heteroaryl, in each case unsubstituted or mono- or polysubstituted, bound via a saturated or unsaturated, branched or unbranched, substituted or unsubstituted $C_{1-4}$ alkyl group;

$R^4$ is selected from the group consisting of H, $C_{1-8}$ alkyl, saturated or unsaturated, branched or unbranched, mono- or polysubstituted or unsubstituted; and —$(CH_2)_o$—W—$(CH_2)_p$—H, wherein
W=O, $NR_7$ or S,
o=0–3, and
p=0–4, and
wherein $R_7$ is selected from the group consisting of H, $C_{1-8}$ alkyl, saturated or unsaturated, branched or unbranched, mono- or polysubstituted or unsubstituted;

$R^5$, if m≠0, is selected from the group consisting of:
—$(CH_2)_qR^{12}$,
—C(Y)-Z-$R^{12}$, and
—C(Y)—O-Z-$R^{12}$,
wherein
Y=O, $CH_2$ or S,
Z=$C_{1-8}$ alkyl, saturated or unsaturated, branched or unbranched, mono- or polysubstituted or unsubstituted, or $(CH_2)_q$, wherein q=0–8, and
$R^{12}$ is selected from the group consisting of H; $C_{3-8}$ cycloalkyl, aryl and heteroaryl, in each case unsubstituted or mono- or polysubstituted; or $R^5$, if m=0, is selected from the group consisting of $C_{3-8}$ cycloalkyl, aryl and heteroaryl, in each case unsubstituted or mono- or polysubstituted, and —$(CH_2)_qR^{12}$, wherein q=0–8, and $R^{12}$ has the meaning given above;

or a pharmaceutically acceptable salt thereof.

2. A compound according to claim 1, wherein said compound is present in the form of a racemate.

3. A compound according to claim 1, wherein said compound is present in the form of a pure stereoisomer or a pure enantiomer or diastereomer.

4. A compound according to claim 1, wherein said compound is present in the form of a mixture of stereoisomers.

5. A cyclohexylurea compound according to claim 1, wherein
$R^1$ and $R^2$ are independently selected from the group consisting of H; and $C_{1-8}$ alkyl, saturated or unsaturated, branched or unbranched, mono- or polysubstituted or unsubstituted; or
$R^1$ and $R^2$ together form a ring and denote $CH_2CH_2OCH_2CH_2$, $CH_2CH_2NR^6CH_2CH_2$, or $(CH_2)_{3-6}$, wherein
$R^6$ is selected from the group consisting of H and $C_{1-8}$ alkyl, saturated or unsaturated, branched or unbranched, mono- or polysubstituted or unsubstituted.

6. A cyclohexylurea compound according to claim 5, wherein $R^1$ and $R^2$ are independently selected from the group consisting of H and $C_{1-4}$ alkyl, saturated or unsaturated, branched or unbranched, mono- or polysubstituted or unsubstituted, or $R^1$ and $R^2$ together form a ring and denote $(CH_2)_{4-5}$.

7. A cyclohexylurea compound according to claim 6, wherein $R^1$ and $R^2$ are independently selected from the group consisting of H, methyl and ethyl.

8. A cyclohexylurea compound according to claim 1, wherein $R^3$ is selected from the group consisting of $C_{3-8}$ cycloalkyl, aryl and heteroaryl, in each case unsubstituted or mono- or polysubstituted; and aryl, $C_{3-8}$ cycloalkyl and heteroaryl, in each case unsubstituted or mono- or polysubstituted, bound via a saturated or unsaturated, unbranched, substituted or unsubstituted $C_{1-2}$ alkyl group.

9. A cyclohexylurea compound according to claim 8, wherein $R^3$ is selected from the group consisting of $C_{5-6}$ cycloalkyl, phenyl, naphthyl, anthracenyl, thiophenyl, benzothiophenyl, furyl, benzofuranyl, benzodioxolanyl, indolyl, indanyl, benzodioxanyl, pyrrolyl, pyrimidiyl and pyrazinyl, in each case unsubstituted or mono- or polysubstituted; and $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl and pyrazinyl, in each case unsubstituted or mono- or polysubstituted, bound via a saturated, unbranched $C_{1-2}$ alkyl group.

10. A cyclohexylurea compound according to claim 9, wherein $R^3$ is selected from the group consisting of phenyl, furyl, thiophenyl, cyclohexanyl, naphthyl, benzofuranyl, indolyl, indanyl, benzodioxanyl, benzodioxolanyl, pyrrolyl, pyrimidiyl, pyrazinyl and benzothiophenyl, in each case unsubstituted or mono- or polysubstituted; and phenyl, furyl and thiophenyl, in each case unsubstituted or mono- or polysubstituted, bound via a saturated, unbranched $C_{1-2}$ alkyl group.

11. A cyclohexylurea compound according to claim 1, wherein $R^4$ is selected from the group consisting of H and $C_{1-8}$ alkyl, saturated or unsaturated, branched or unbranched, mono- or polysubstituted or unsubstituted.

12. A cyclohexylurea compound according to claim 11, wherein $R^4$ is H, $CH_3$ or $C_2H_5$.

13. A cyclohexylurea compound according to claim 1, wherein $R_1$ and $R_2$ are independently selected from the group consisting of H, $CH_3$, $C_2H_5$ and CHO.

14. A cyclohexylurea compound according to claim 13, wherein $R_1$ and $R_2$ are independently selected from the group consisting of H and $CH_3$.

15. A cyclohexylurea compound according to claim 1, wherein $R_3$ is selected from the group consisting of indolyl, pyridyl, thienyl, pyrrolyl, phenyl, benzyl and phenethyl, in each case unsubstituted or mono- or polysubstituted on the ring.

16. A cyclohexylurea compound according to claim 15, wherein $R_3$ is selected from the group consisting of phenyl which is unsubstituted or mono-substituted on the ring, benzyl, phenethyl, indolyl, pyridyl, thienyl, and pyrrolyl.

17. A cyclohexylurea compound according to claim 16, wherein $R_3$ is selected from the group consisting of phenyl, benzyl, phenethyl, o-fluorophenyl, m-fluorophenyl, p-fluorophenyl, o-chlorophenyl, p-chlorophenyl, m-chlorophenyl, o-bromophenyl, m-bromophenyl, p-bromophenyl, o-iodophenyl, m-iodophenyl, p-iodophenyl, o-aminophenyl, m-aminophenyl, p-aminophenyl, o-methylphenyl, m-methylphenyl, p-methylphenyl, o-methoxyphenyl, m-methoxyphenyl, p-methoxyphenyl, o-ethylphenyl, m-ethylphenyl, p-ethylphenyl, o-ethoxyphenyl, m-ethoxyphenyl, p-ethoxyphenyl, o-hydroxyphenyl, m-hydroxyphenyl, p-hydroxyphenyl, indolyl, pyridyl, thienyl, and pyrrolyl.

18. A cyclohexylurea compound according to claim 1, wherein $R_4$ is selected from the group consisting of H, $CH_3$, $C_2H_5$, n-propyl, i-propyl, n-butyl, i-butyl and t-butyl.

19. A cyclohexylurea compound according to claim 1, wherein m≠0, and
$R_5$ is selected from the group consisting of:
—$(CH_2)_qR^{12}$,
—C(Y)-Z-$R^{12}$, and
—C(Y)—O-(Z)-$R^{12}$, wherein
Y=O, and
Z=$C_{1-8}$ alkyl, saturated or unsaturated, branched or unbranched, mono- or polysubstituted or unsubstituted; or $(CH_2)_q$, wherein q=0-8.

20. A cyclohexylurea compound according to claim 19, wherein Z=$C_{1-6}$ alkyl, saturated or unsaturated, branched or unbranched, mono- or polysubstituted or unsubstituted; or $(CH_2)_q$ in which q=0-6.

21. A cyclohexylurea compound according to claim 1, wherein m=0, and
R$_5$ is —$(CH_2)_qR_{12}$, in which q=0-6.

22. A cyclohexylurea compound according to claim 1, wherein $R^{12}$ is H or a radical selected from the group consisting of cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidiyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl and quinazolinyl, in each case unsubstituted or mono- or polysubstituted.

23. A cyclohexylurea compound according to claim 22, wherein $R^{12}$ is H or a radical selected from the group consisting of cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl and pyrimidiyl, in each case unsubstituted or mono- or polysubstituted.

24. A cyclohexylurea compound according to claim 1, wherein said compound is selected from the group consisting of:
- 1-(4-dimethylamino-4-phenylcyclohexyl)-3-(3-phenylpropyl)urea hydrochloride (more nonpolar and more polar diastereoisomer);
- 1-(4-dimethylamino-4-phenylcyclohexyl)-3-[2-(1H-indol-3-yl)ethyl]urea hydrochloride (more nonpolar and more polar diastereoisomer);
- N-[(4-dimethylamino-4-phenylcyclohexylcarbamoyl)methyl]-3-(1H-indol-3-yl)butyramide hydrochloride (more nonpolar and more polar diastereoisomer);
- 5-(1H-indol-3-yl)-pentanoic acid [(4-dimethylamino-4-phenylcyclohexyl-carbamoyl)methyl]amide hydrochloride (more nonpolar and more polar diastereoisomer);
- 6-(1H-indol-3-yl)hexanoic acid [(4-dimethylamino-4-phenylcyclohexyl-carbamoyl)-methyl]-amide hydrochloride (more nonpolar and more polar diastereoisomer);
- N-[(4-dimethylamino-4-phenylcyclohexylcarbamoyl)methyl]-3-(1H-indol-3-yl)propionamide hydrochloride (more nonpolar and more polar diastereoisomer);
- N-(4-dimethylamino-4-phenylcyclohexyl)-2-(2-1H-indol-3-ylacetylamino)-propionamide hydrochloride (more nonpolar and more polar diastereoisomer);
- 2-(2-1H-indol-3-ylacetylamino)-4-methylpentanoic acid (4-dimethylamino-4-phenylcyclohexyl)amide hydrochloride (more nonpolar and more polar diastereoisomer);
- 1-(4-dimethylamino-4-phenylcyclohexyl)-3-[2-(1H-indol-3-yl)-1-methyl-ethyl]-urea hydrochloride (more nonpolar and more polar diastereoisomer);
- 1-(4-dimethylamino-4-phenylcyclohexyl)-3-[2-(5-fluoro-1H-indol-3-yl)ethyl]-urea hydrochloride (more nonpolar and more polar diastereoisomer);
- 1-(4-dimethylamino-4-phenylcyclohexylmethyl)-3-[2-(1H-indol-3-yl)ethyl]-urea hydrochloride (more nonpolar and more polar diastereoisomer);
- 1-(4-dimethylamino-4-phenylcyclohexylmethyl)-3-(3-phenylpropyl)urea hydrochloride (more nonpolar and more polar diastereoisomer);
- 1-(4-dimethylamino-4-phenylcyclohexylmethyl)-3-[2-(1H-indol-3-yl)-1-methyl-ethyl]-urea hydrochloride (more nonpolar and more polar diastereoisomer);
- 1-(4-dimethylamino-4-phenylcyclohexylmethyl)-3-[2-(5-fluoro-1H-indol-3-yl)ethyl]urea citrate (more nonpolar and more polar diastereoisomer);
- 1-[3-(4-dimethylamino-4-phenyl-cyclohexyl)-propyl]-3-[2-(1H-indol-3-yl)-ethyl]-urea (more nonpolar and more polar diastereoisomer);
- 1-(4-dimethylamino-4-phenylcyclohexyl)-3-(4-phenylpropyl)thiourea citrate (more nonpolar and more polar diastereoisomer);
- 1-(4-dimethylamino-4-phenylcyclohexyl)-3-[2-(1H-indol-3-yl)methyl-ethyl]thiourea citrate (more nonpolar and more polar diastereoisomer);
- 1-[3-(4-dimethylamino-4-phenyl-cyclohexyl)-propyl]-3-[2-(1H-indol-3-yl)-ethyl]-urea (more nonpolar and more polar diastereoisomer);
- 1-(4-dimethylamino-4-phenylcyclohexyl methyl)-3-[2-(1H-indol-3-yl)ethyl]-thiourea citrate (more nonpolar and more polar diastereoisomer);
- 1-(4-dimethylamino-4-phenylcyclohexylmethyl)-3-[2-(1H-indol-3-yl)-1-methylethyl]thiourea citrate (more nonpolar and more polar diastereoisomer);
- 2-[3-(4-dimethylamino-4-phenylcyclohexylmethyl)thioureido]-3-(1H-indol-3-yl)propionic acid methyl ester citrate (more nonpolar and more polar diastereoisomer);
- 1-[2-(4-dimethylamino-4-phenylcyclohexyl)ethyl]-3-[2-(1H-indol-3-yl)-ethyl]thiourea hydrochloride (more nonpolar diastereoisomer); and
- 1-[2-(4-dimethylamino-4-phenylcyclohexyl)ethyl]-3-[2-(1H-indol-3-yl)-ethyl]thiourea citrate (more polar diastereoisomer).

25. A pharmaceutical composition comprising at least one cyclohexylurea compound according to claim 1, and at least one additional substance selected from the group consisting of pharmaceutical additives, pharmaceutical auxiliary substances, and other pharmaceutical active ingredients.

* * * * *